(12) United States Patent
Li et al.

(10) Patent No.: US 11,161,904 B2
(45) Date of Patent: Nov. 2, 2021

(54) ANTI-PD-1 ANTIBODY AND USE THEREOF

(71) Applicant: AMPSOURCE BIOPHARMA SHANGHAI INC., Shanghai (CN)

(72) Inventors: Qiang Li, Shanghai (CN); Yuncheng Zheng, Shanghai (CN); Lu Yang, Shanghai (CN); Xinlu Ma, Shanghai (CN); Yuanli Li, Shanghai (CN)

(73) Assignee: AMPSOURCE BIOPHARMA SHANGHAI INC., Shanghai (CN)

( * ) Notice: Subject to any disclaimer, the term of this patent is extended or adjusted under 35 U.S.C. 154(b) by 186 days.

(21) Appl. No.: 16/471,909

(22) PCT Filed: Jul. 6, 2017

(86) PCT No.: PCT/CN2017/092026
§ 371 (c)(1),
(2) Date: Jun. 20, 2019

(87) PCT Pub. No.: WO2018/113258
PCT Pub. Date: Jun. 28, 2018

(65) Prior Publication Data
US 2019/0367617 A1    Dec. 5, 2019

(30) Foreign Application Priority Data
Dec. 22, 2016 (CN) .......................... 201611198440.8

(51) Int. Cl.
*C07K 16/28* (2006.01)
*A61K 47/55* (2017.01)
*C07K 16/22* (2006.01)
*C07K 16/32* (2006.01)
*C07K 16/46* (2006.01)

(52) U.S. Cl.
CPC .......... *C07K 16/2818* (2013.01); *A61K 47/55* (2017.08); *C07K 16/22* (2013.01); *C07K 16/2863* (2013.01); *C07K 16/2878* (2013.01); *C07K 16/2887* (2013.01); *C07K 16/32* (2013.01); *C07K 16/468* (2013.01)

(58) Field of Classification Search
CPC ............................ C07K 16/2818; C07K 16/22; C07K 16/2863; C07K 16/2878; C07K 16/2887; C07K 16/32; C07K 16/468; A61K 47/55
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 5,225,539 A | 7/1993 | Winter | |
| 5,260,203 A | 11/1993 | Ladner et al. | |
| 5,530,101 A | 6/1996 | Queen et al. | |
| 5,585,089 A | 12/1996 | Queen et al. | |
| 5,693,762 A | 12/1997 | Queen et al. | |
| 6,180,370 B1 | 1/2001 | Queen et al. | |

FOREIGN PATENT DOCUMENTS

| | | | | |
|---|---|---|---|---|
| CN | 102482347 A | 5/2012 | | |
| CN | 101213297 B | 2/2013 | | |
| CN | 104470949 A | 3/2015 | | |
| CN | 104945508 B | 9/2015 | | |
| CN | 105339389 A | 2/2016 | | |
| CN | 105531288 A | 4/2016 | | |
| CN | 105683217 A | 6/2016 | | |
| CN | 106519034 A | 3/2017 | | |
| WO | WO1988001649 A1 | 3/1988 | | |
| WO | WO2002043478 A2 | 6/2002 | | |
| WO | WO-2006121168 A1 | * | 11/2006 | ......... C07K 16/2818 |
| WO | WO2016104688 A1 | 6/2016 | | |
| WO | WO2017011580 A3 | 1/2017 | | |

OTHER PUBLICATIONS

Barber D L et al. "Restoring function in exhausted CD8 T cells during chronic viral infection", Nature, 2006, 439(7077): 682.
Chothia C et al, "Canonical Structures for the Hypervariable Regions of Immunoglobulins", J Mol Biol, 1987, 196(4):901-917.
Davies D R et al, "Antibody-Antigen Complexes", Annu. Rev. Biochem, 1990, 59(1):439-473.
Dong H et al. "Tumor-associated B7-H1 promotes T-cell apoptosis: A potential mechanism of immune evasion", Nature Medicine, 2002, 8(8):793-800.
Francisco L M et al, "The PD-1 pathway in tolerance and autoimmunity," Immunological reviews, 2010, 236(1): 219-242.
Hamid O et al, "Anti-programmed death-1 and anti-programmed death-ligand 1 antibodies in cancer therapy", Expert opinion on biological therapy, 2013, 13(6): 847-861.
Holliger P et al, "Engineered antibody fragments and the rise of single domains", Nature biotechnology, 2005, 23(9):1126.
Köhler G et al, "Continuous cultures of fused cells secreting antibody of predefined specificity", Nature, 1975, 256(5517): 495.
Latchman Y et al, "PD-L2 is a second ligand for PD-1 and inhibits T cell activation", Nature immunology, 2001, 2(3):261.
Lonberg N et al, "Antigen-specific human antibodies from mice comprising four distinct genetic modifications", Nature, 1994, 368(6474):856-859.

(Continued)

*Primary Examiner* — Brad Duffy
*Assistant Examiner* — Cheom-Gil Cheong
(74) *Attorney, Agent, or Firm* — Finnegan, Henderson, Farabow, Garrett & Dunner LLP

(57) ABSTRACT

This disclosure provides an antibody specifically binding to PD-1 with high affinity. Also provided are a nucleic acid molecule for coding the antibody, an expression vector and a host cell for expressing the antibody, and a production method for the antibody. In addition, also provided are an immunoconjugate and a pharmaceutical composition comprising the antibody and use of the antibody in preparation of drugs for treating cancers, infectious diseases, and inflammatory diseases.

Figure 1:
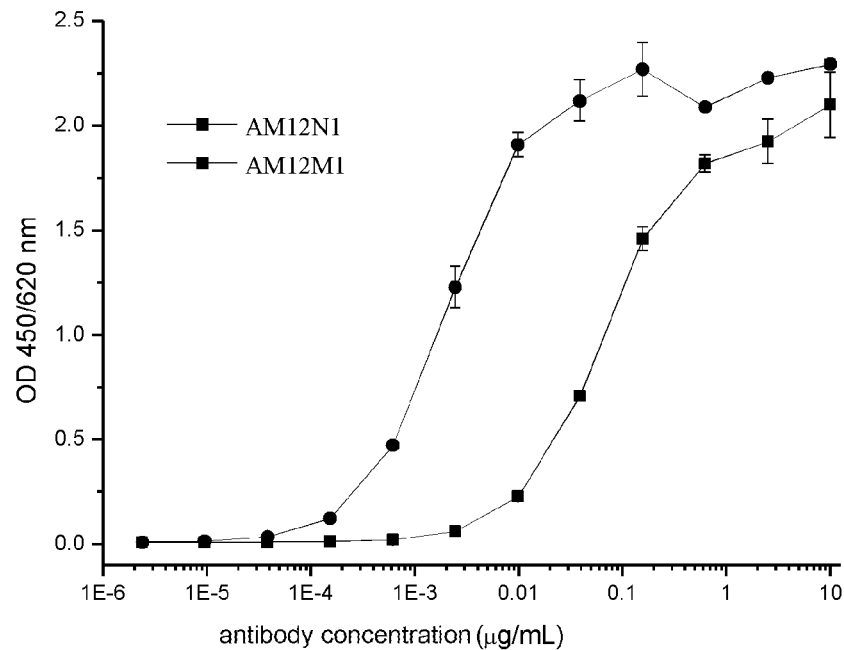

27 Claims, 8 Drawing Sheets
Specification includes a Sequence Listing.

(56) References Cited

OTHER PUBLICATIONS

Malmqvist M. "Biospecific interaction analysis using biosensor technology", Nature, 1993, 361(6408): 186-187.

Marasco W A et al, "Design, intracellular expression, and activity of a human anti-human immunodeficiency virus type 1 gp120 single-chain antibody", Proc Natl Acad Sci USA, 1993, 90(16): 7889-7893.

Okazaki T et al, "PD-1 and PD-1 ligands: from discovery to clinical application", International immunology, 2007, 19(7): 813-824.

Shimauchi T et al, "Augmented expression of programmed death-1 in both neoplastic and non-neoplastic CD41 T-cells in adult T-cell leukemia/lymphoma", Int J Cancer, 2007, 121(12):2585-2590.

Venkatachari N J et al, "Human immunodeficiency virus (HIV-1) infection selectively downregulates PD-1 expression in infected cells and protects the cells from early apoptosis in vitro and in vivo", Virology, 2008, 376(1): 140-153.

Yao S et al, "Advances in targeting cell surface signalling molecules for immune modulation", Nature reviews Drug discovery, 2013, 12(2):130.

International Search Report of PCT/CN2017/092026, dated Sep. 20, 2017.

Addeo R et al, Pembrolizumab: the value of PDL1 biomarker in head and neck cancer, *Expert Opinion on Biological Therapy*, 2016, vol. 16 (9), pp. 1075-1078.

Extended European Search Report for EP17885356.0, dated Mar. 17, 2021.

\* cited by examiner

SEQUENCE LISTING

```
<160> NUMBER OF SEQ ID NOS: 42

<210> SEQ ID NO 1
<211> LENGTH: 8
<212> TYPE: PRT
<213> ORGANISM: Artificial Sequence
<220> FEATURE:
<223> OTHER INFORMATION: CDR-H1

<400> SEQUENCE: 1

Gly Phe Thr Phe Ser Ser Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: CDR-H1

<400> SEQUENCE: 2

Gly Ile Thr Phe Ser Asn Ser Gly
1               5

<210> SEQ ID NO 3
<211> LENGTH: 8
<212> TYPE: PRT
<213> ORGANISM: Artificial Sequence
<220> FEATURE:
<223> OTHER INFORMATION: CDR-H2

<400> SEQUENCE: 3

Ile Ser Gly Gly Gly Arg Asp Thr
1               5

<210> SEQ ID NO 4
<211> LENGTH: 7
<212> TYPE: PRT
<213> ORGANISM: Artificial Sequence
<220> FEATURE:
<223> OTHER INFORMATION: CDR-H2

<400> SEQUENCE: 4

Trp Tyr Asp Gly Ser Lys Arg
1               5

<210> SEQ ID NO 5
<211> LENGTH: 11
<212> TYPE: PRT
<213> ORGANISM: Artificial Sequence
<220> FEATURE:
<223> OTHER INFORMATION: CDR-H3

<400> SEQUENCE: 5

Ala Arg Gln Lys Asp Thr Ser Trp Phe Val His
1               5                   10

<210> SEQ ID NO 6
<211> LENGTH: 6
<212> TYPE: PRT
<213> ORGANISM: Artificial Sequence
<220> FEATURE:
<223> OTHER INFORMATION: CDR-H3

<400> SEQUENCE: 6

Ala Thr Asn Asp Asp Tyr
1               5
```

```
<210> SEQ ID NO 7
<211> LENGTH: 10
<212> TYPE: PRT
<213> ORGANISM: Artificial Sequence
<220> FEATURE:
<223> OTHER INFORMATION: CDR-L1

<400> SEQUENCE: 7

Glu Ser Val Asp Asp Tyr Gly Ile Ser Phe
1               5                   10

<210> SEQ ID NO 8
<211> LENGTH: 6
<212> TYPE: PRT
<213> ORGANISM: Artificial Sequence
<220> FEATURE:
<223> OTHER INFORMATION: CDR-L1

<400> SEQUENCE: 8

Gln Ser Val Ser Ser Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: mAb1 CDR-L2

<400> SEQUENCE: 9

Val Ala Ser
1

<210> SEQ ID NO 10
<211> LENGTH: 3
<212> TYPE: PRT
<213> ORGANISM: Artificial Sequence
<220> FEATURE:
<223> OTHER INFORMATION: CDR-L2

<400> SEQUENCE: 10

Asp Ala Ser
1

<210> SEQ ID NO 11
<211> LENGTH: 9
<212> TYPE: PRT
<213> ORGANISM: Artificial Sequence
<220> FEATURE:
<223> OTHER INFORMATION: CDR-L3

<400> SEQUENCE: 11

Gln Gln Ser Lys Glu Val Pro Trp Thr
1               5

<210> SEQ ID NO 12
<211> LENGTH: 9
<212> TYPE: PRT
<213> ORGANISM: Artificial Sequence
<220> FEATURE:
<223> OTHER INFORMATION: CDR-L3

<400> SEQUENCE: 12

Gln Gln Ser Ser Asn Trp Pro Arg Thr
1               5
```

```
<210> SEQ ID NO 13
<211> LENGTH: 118
<212> TYPE: PRT
<213> ORGANISM: Artificial Sequence
<220> FEATURE:
<223> OTHER INFORMATION: Amino acid sequence of the heavy chain variable
      region of the murine antibody AB12M1 or the chimeric antibody
      AB12M2

<400> SEQUENCE: 13

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Gln Lys Asp Thr Ser Trp Phe Val His Trp Gly Gln Gly Thr
            100                 105                 110

Leu Val Thr Val Ser Ala
        115

<210> SEQ ID NO 14
<211> LENGTH: 111
<212> TYPE: PRT
<213> ORGANISM: Artificial Sequence
<220> FEATURE:
<223> OTHER INFORMATION: Amino acid sequence of the light chain variable
      region of the murine antibody AB12M1 or the chimeric antibody
      AB12M2

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Amino acid sequence of the heavy chain variable
      region of the murine antibody AB12N1 or the chimeric antibody
      AB12N2
```

<400> SEQUENCE: 15

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val
            100                 105                 110

<210> SEQ ID NO 16
<211> LENGTH: 107
<212> TYPE: PRT
<213> ORGANISM: Artificial Sequence
<220> FEATURE:
<223> OTHER INFORMATION: Amino acid sequence of the light chain variable region of the murine antibody AB12N1 or the chimeric antibody AB12N2

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 17
<211> LENGTH: 118
<212> TYPE: PRT
<213> ORGANISM: Artificial Sequence
<220> FEATURE:
<223> OTHER INFORMATION: Amino acid sequence of the heavy chain variable region of humanized antibody AB12M3

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Ser Val
    50                  55                  60

```
Lys Gly Arg Phe Thr Ile Ser Arg Asp Asn Ala Lys Asn Asn Leu Tyr
 65                  70                  75                  80

Leu Gln Met Asn Ser Leu Arg Ala Glu Asp Thr Ala Leu Tyr Tyr Cys
                 85                  90                  95

Ala Arg Gln Lys Asp Thr Ser Trp Phe Val His Trp Gly Gln Gly Thr
            100                 105                 110

Leu Val Thr Val Ser Ser
        115
```

<210> SEQ ID NO 18
<211> LENGTH: 111
<212> TYPE: PRT
<213> ORGANISM: Artificial Sequence
<220> FEATURE:
<223> OTHER INFORMATION: Amino acid sequence of the light chain variable
      region of humanized antibody AB12M3

<400> SEQUENCE: 18

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Asp Tyr
             20                  25                  30

Gly Ile Ser Phe Met Asn Trp Phe Gln Gln Lys Pro Gly Gln Ala Pro
         35                  40                  45

Lys Leu Leu Ile Tyr Val Ala Ser Asn Gln Gly Ser Gly Val Pro Ala
 50                  55                  60

Arg Phe Ser Gly Ser Gly Ser Gly Thr Asp Phe Ser Leu Thr Ile Ser
 65                  70                  75                  80

Ser Leu Glu Pro Asp Asp Thr Ala Met Tyr Phe Cys Gln Gln Ser Lys
                 85                  90                  95

Glu Val Pro Trp Thr Phe Gly Gly Gly Thr Lys Val Glu Ile Lys
            100                 105                 110
```

<210> SEQ ID NO 19
<211> LENGTH: 118
<212> TYPE: PRT
<213> ORGANISM: Artificial Sequence
<220> FEATURE:
<223> OTHER INFORMATION: Amino acid sequence of the heavy chain variable
      region of humanized antibody AB12M4

<400> SEQUENCE: 19

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Gly Met Ser Trp Val Arg Gln Thr Pro Glu Lys Arg Leu Glu Trp Val
         35                  40                  45

Ala Thr Ile Ser Gly Gly Gly Arg Asp Thr Tyr Tyr Pro Asp Ser Val
 50                  55                  60

Lys Gly Arg Phe Thr Ile Ser Arg Asp Asn Ala Lys Asn Asn Leu Tyr
 65                  70                  75                  80

Leu Gln Met Ser Ser Leu Arg Ser Glu Asp Thr Ala Leu Tyr Tyr Cys
                 85                  90                  95

Ala Arg Gln Lys Asp Thr Ser Trp Phe Val His Trp Gly Gln Gly Thr
            100                 105                 110

Leu Val Thr Val Ser Ser
        115
```

```
<210> SEQ ID NO 20
<211> LENGTH: 111
<212> TYPE: PRT
<213> ORGANISM: Artificial Sequence
<220> FEATURE:
<223> OTHER INFORMATION: Amino acid sequence of the light chain variable
      region of humanized antibody AB12M4

<400> SEQUENCE: 20

Glu Ile Val Leu Thr Gln Ser Pro Ala Thr Leu Ala Val Ser Pro Gly
1               5                   10                  15

Glu Arg Ala Thr Ile Ser Cys Arg Ala Ser Glu Ser Val Asp Asp Tyr
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Asn Gln Gly Ser Gly Val Pro Ala
    50                  55                  60

Arg Phe Ser Gly Ser Gly Ser Gly Thr Asp Phe Thr Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
                100                 105                 110

<210> SEQ ID NO 21
<211> LENGTH: 118
<212> TYPE: PRT
<213> ORGANISM: Artificial Sequence
<220> FEATURE:
<223> OTHER INFORMATION: Amino acid sequence of the heavy chain variable
      region of humanized antibody AB12M5

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ala Ile Ser Gly Gly Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Asp Thr Ser Trp Phe Val His Trp Gly Gln Gly Thr
                100                 105                 110

Met Val Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12M5

<400> SEQUENCE: 22

Glu Ile Val Leu Thr Gln Ser Pro Ala Thr Leu Ser Leu Ser Pro Gly
```

```
            1               5                  10                 15
         Glu Arg Ala Thr Leu Ser Cys Arg Ala Ser Glu Ser Val Asp Asp Tyr
                        20                 25                 30

Gly Ile Ser Phe Leu Ala Trp Tyr Gln Gln Lys Pro Gly Gln Ala Pro
                        35                 40                 45

Arg Val Ala Ser Asn Arg Ala Thr Gly Ile Pro Ala Arg Phe Ser Gly
                50                 55                 60

Ser Gly Pro Gly Thr Asp Phe Thr Leu Thr Ile Ser Ser Leu Glu Pro
         65                 70                 75                 80

Glu Asp Phe Ala Val Tyr Tyr Cys Gln Gln Ser Lys Glu Val Pro Trp
                        85                 90                 95

Thr Phe Gly Gly Gly Thr Lys Val Glu Ile Lys
                        100                105

<210> SEQ ID NO 23
<211> LENGTH: 118
<212> TYPE: PRT
<213> ORGANISM: Artificial Sequence
<220> FEATURE:
<223> OTHER INFORMATION: Amino acid sequence of the heavy chain variable
      region of humanized antibody AB12M6

<400> SEQUENCE: 23

Glu Val Gln Leu Val Glu Ser Gly Gly Gly Leu Val Gln Pro Gly Gly
         1               5                  10                 15

Ser Leu Arg Leu Ser Cys Ala Ala Ser Gly Phe Thr Phe Ser Ser Tyr
                        20                 25                 30

Gly Met Ser Trp Val Arg Gln Ala Pro Glu Lys Gly Leu Glu Trp Val
                        35                 40                 45

Ser Ala Ile Ser Gly Gly Gly Arg Asp Thr Tyr Tyr Ala Asp Ser Val
                50                 55                 60

Lys Gly Arg Phe Thr Ile Ser Arg Asp Asn Ser Lys Asn Thr Leu Tyr
         65                 70                 75                 80

Leu Gln Met Asn Ser Leu Arg Ala Glu Asp Thr Ala Val Tyr Tyr Cys
                        85                 90                 95

Ala Arg Gln Lys Asp Thr Ser Trp Phe Val His Trp Gly Gln Gly Thr
                        100                105                110

Met Val Thr Val Ser Ser
                 115

<210> SEQ ID NO 24
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12M6

<400> SEQUENCE: 24

Glu Ile Val Leu Thr Gln Ser Pro Ala Thr Leu Ser Leu Ser Pro Gly
         1               5                  10                 15

Glu Arg Ala Thr Leu Ser Cys Arg Ala Ser Glu Ser Val Asp Asp Tyr
                        20                 25                 30

Gly Ile Ser Phe Leu Ala Trp Phe Gln Gln Lys Pro Gly Gln Ala Pro
                        35                 40                 45

Arg Val Ala Ser Asn Arg Ala Ser Gly Ile Pro Ala Arg Phe Ser Gly
                50                 55                 60

Ser Gly Pro Gly Thr Asp Phe Thr Leu Thr Ile Ser Ser Leu Glu Pro
```

```
                65                  70                  75                  80
Glu Asp Phe Ala Val Tyr Tyr Cys Gln Gln Ser Lys Glu Val Pro Trp
                    85                  90                  95

Thr Phe Gly Gly Gly Thr Lys Val Glu Ile Lys
            100                 105

<210> SEQ ID NO 25
<211> LENGTH: 118
<212> TYPE: PRT
<213> ORGANISM: Artificial Sequence
<220> FEATURE:
<223> OTHER INFORMATION: Amino acid sequence of the heavy chain variable
      region of humanized antibody AB12M7

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Glu Lys Gly Leu Glu Trp Val
        35                  40                  45

Ser Ala Ile Ser Gly Gly Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Asp Thr Ser Trp Phe Val His Trp Gly Gln Gly Thr
            100                 105                 110

Met Val Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12M7

<400> SEQUENCE: 26

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asp Tyr
            20                  25                  30

Gly Ile Ser Phe Leu Ala Trp Phe Gln Gln Lys Pro Gly Gln Ala Pro
        35                  40                  45

Arg Val Ala Ser Asn Arg Ala Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Asp Asp Phe Ala Val Tyr Tyr Cys Gln Gln Ser Lys Glu Val Pro Trp
                85                  90                  95

Thr Phe Gly Gly Gly Thr Lys Val Glu Ile Lys
            100                 105

<210> SEQ ID NO 27
<211> LENGTH: 118
<212> TYPE: PRT
```

<213> ORGANISM: Artificial Sequence
<220> FEATURE:
<223> OTHER INFORMATION: Amino acid sequence of the heavy chain variable region of humanized antibody AB12M8

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Glu Lys Gly Leu Glu Trp Val
        35                  40                  45

Ser Ala Ile Ser Gly Gly Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Asp Thr Ser Trp Phe Val His Trp Gly Gln Gly Thr
            100                 105                 110

Met Val Thr Val Ser Ser
        115
```

<210> SEQ ID NO 28
<211> LENGTH: 107
<212> TYPE: PRT
<213> ORGANISM: Artificial Sequence
<220> FEATURE:
<223> OTHER INFORMATION: Amino acid sequence of the light chain variable region of humanized antibody AB12M8

<400> SEQUENCE: 28

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Tyr
            20                  25                  30

Gly Ile Ser Phe Leu Ala Trp Tyr Gln Gln Lys Pro Gly Gln Ala Pro
        35                  40                  45

Arg Val Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Asp Asp Phe Ala Val Tyr Tyr Cys Gln Gln Ser Lys Glu Val Pro Trp
                85                  90                  95

Thr Phe Gly Gly Gly Thr Lys Val Glu Ile Lys
            100                 105
```

<210> SEQ ID NO 29
<211> LENGTH: 118
<212> TYPE: PRT
<213> ORGANISM: Artificial Sequence
<220> FEATURE:
<223> OTHER INFORMATION: Amino acid sequence of the heavy chain variable region of humanized antibody AB12M9

<400> SEQUENCE: 29

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Gly Met Ser Trp Val Arg Gln Ala Pro Glu Lys Gly Leu Glu Trp Val
            35                  40                  45

Ser Ala Ile Ser Gly Gly Arg Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Arg Gln Lys Asp Thr Ser Trp Phe Val His Trp Gly Gln Gly Thr
            100                 105                 110

Met Val Thr Val Ser Ser
            115

<210> SEQ ID NO 30
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12M9

<400> SEQUENCE: 30

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Asp Tyr
                 20                  25                  30

Gly Ile Ser Phe Leu Ala Trp Tyr Gln Gln Lys Pro Gly Gln Ala Pro
            35                  40                  45

Arg Val Ala Ser Asn Arg Ala Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Asp Asp Phe Ala Val Tyr Tyr Cys Gln Gln Ser Lys Glu Val Pro Trp
                 85                  90                  95

Thr Phe Gly Gly Gly Thr Lys Val Glu Ile Lys
            100                 105

<210> SEQ ID NO 31
<211> LENGTH: 110
<212> TYPE: PRT
<213> ORGANISM: Artificial Sequence
<220> FEATURE:
<223> OTHER INFORMATION: Amino acid sequence of the heavy chain variable
      region of humanized antibody AB12N3

<400> SEQUENCE: 31

Gln Val Gln Leu Val Glu Ser Gly Gly Gly Val Val Gln Pro Gly Arg
 1               5                  10                  15

Ser Leu Arg Leu Ser Cys Ala Ala Ser Gly Ile Thr Phe Ser Asn Ser
                 20                  25                  30

Gly Met His Trp Val Arg Gln Ala Pro Gly Lys Gly Leu Glu Trp Val
            35                  40                  45

Ala Val Trp Tyr Asp Gly Ser Lys Arg Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95
```

Thr Asn Asp Asp Tyr Trp Gly Gln Gly Thr Leu Val Thr Val
            100                 105                 110

<210> SEQ ID NO 32
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12N3

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 33
<211> LENGTH: 111
<212> TYPE: PRT
<213> ORGANISM: Artificial Sequence
<220> FEATURE:
<223> OTHER INFORMATION: Amino acid sequence of the heavy chain variable
      region of humanized antibody AB12N4

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val
            100                 105                 110

<210> SEQ ID NO 34
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12N4

<400> SEQUENCE: 34

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

```
<210> SEQ ID NO 35
<211> LENGTH: 110
<212> TYPE: PRT
<213> ORGANISM: Artificial Sequence
<220> FEATURE:
<223> OTHER INFORMATION: Amino acid sequence of the heavy chain variable
      region of humanized antibody AB12N5

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Trp Tyr Asp Gly Ser Lys Arg Tyr Tyr Ala Asp Ser Val Lys
        50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Thr Asn Asp Asp Tyr Trp Gly Gln Gly Thr Leu Val Thr Val
            100                 105                 110
```

```
<210> SEQ ID NO 36
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized antibody AB12N5

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Ser Ser Asn Trp Pro Arg
            85                  90                  95

Thr Phe Gly Gln Gly Thr Lys Val Glu Ile Lys
            100                 105

<210> SEQ ID NO 37
<211> LENGTH: 354
<212> TYPE: DNA
<213> ORGANISM: Artificial Sequence
<220> FEATURE:
<223> OTHER INFORMATION: Nucleotide sequence of the heavy chain variable
      region of the chimeric antibody AB12M2

<400> SEQUENCE: 37
gaggtgaagc tggtggagag cggaggagga ctggtgaagc aggaggatc tctgaagctg      60 agctgtgctg cctctggctt cacctttcc tcttacggca tgagctgggt gagacagaca     120
cccgagaagc gcctggaatg ggtcgctacc atctctggcg gcggcagaga cacatactat     180
cctgattccg tgaagggcag attccacatc agccgcgata cgccaaaaa taatctgtat     240 ctgcaaatgt cttccctgag gtctgaggac accgctctgt actattgcgc ccggcagaag     300
gatacatctt ggttcgtgca ctggggacag ggcaccctgg tgaccgtgtc cgcc           354

<210> SEQ ID NO 38
<211> LENGTH: 333
<212> TYPE: DNA
<213> ORGANISM: Artificial Sequence
<220> FEATURE:
<223> OTHER INFORMATION: Nucleotide sequence of the light chain variable
      region of the chimeric antibody AB12M2

<400> SEQUENCE: 38
gacatcgtgc tgacccagtc tccagctagc ctggccgtgt ccctgggaca gagggctacc      60
atcagctgtc gggcctctga gtctgtcgac gattacggca tctctttcat gaattggttc     120
cagcagaaac ctggccagcc ccctaaactg ctgatctatg tcgcttccaa tcagggaagc     180
ggagtgcctg ctagattcag cggatctgga tctggaaccg acttcagcct gaacatccat     240
ccaatggagg aggacgatac cgccatgtac ttctgtcagc agtctaaaga agtcccttgg     300
acctttggcg gcggcacaaa gctggagatc aag                                  333

<210> SEQ ID NO 39
<211> LENGTH: 354
<212> TYPE: DNA
<213> ORGANISM: Artificial Sequence
<220> FEATURE:
<223> OTHER INFORMATION: Nucleotide sequence of the heavy chain variable
      region of humanized antibody AB12M3

<400> SEQUENCE: 39
gaggtgcagc tggtggagtc cggaggagga ctggtgcagc ctggaggcag cctgagactg      60
tcttgcgccg cttccggctt cacctttcc agctacggca tgtcttgggt gagacaggct     120
cctggcaagg gactggagtg ggtggctacc atctccggag gaggaaggga cacatactat     180
ccagatagcg tgaagggcag gttcacaatc tctcgggaca cgctaagaa caatctgtat     240 ctgcagatga actccctgag agctgaggac accgccctgt actattgcgc ccggcagaag     300
gatacaagct ggtttgtgca ctggggccag ggcaccctgg tgacagtgtc ttcc           354

<210> SEQ ID NO 40
<211> LENGTH: 333
<212> TYPE: DNA

-continued

```
<213> ORGANISM: Artificial Sequence
<220> FEATURE:
<223> OTHER INFORMATION: Nucleotide sequence of the light chain variable
      region of humanized antibody AB12M3

<400> SEQUENCE: 40
gagatcgtgc tgacccagag ccctgccaca ctgagcctgt ctccaggcga gagggctacc        60
ctgtcttgtc gggcctccga gagcgtggac gattacggca tctccttcat gaactggttt       120
cagcagaagc caggccaggc tcccaagctg ctgatctatg tggccagcaa tcagggctct       180
ggagtgccag ctcgcttctc tggctccgga agcggaaccg acttttctct gacaatcagc       240
tctctggagc cagacgatac agccatgtac ttctgccagc agtccaagga ggtgccatgg       300
acctttggcg aggaacaaa ggtggagatc aag                                      333

<210> SEQ ID NO 41
<211> LENGTH: 354
<212> TYPE: DNA
<213> ORGANISM: Artificial Sequence
<220> FEATURE:
<223> OTHER INFORMATION: Nucleotide sequence of the heavy chain variable
      region of humanized antibody AB12M4

<400> SEQUENCE: 41
gaggtgcagc tggtggagag cggaggagga ctggtgaagc caggaggatc tctgaggctg        60
agctgtgctg cctctggctt cacctttttcc tcttacggca tgagctgggt gagacagaca      120
cccgagaagc gcctggaatg ggtcgctacc atctctggcg gcggcagaga cacatactat       180
cctgattccg tgaagggcag attcaccatc agccgcgata cgccaaaaa taatctgtat        240 ctgcaaatgt cttccctgag gtctgaggac accgctctgt actattgcgc ccggcagaag       300
gatacatctt ggttcgtgca ctggggacag ggcaccctgg tgaccgtgtc ctcc             354

<210> SEQ ID NO 42
<211> LENGTH: 333
<212> TYPE: DNA
<213> ORGANISM: Artificial Sequence
<220> FEATURE:
<223> OTHER INFORMATION: Nucleotide sequence of the light chain variable
      region of humanized antibody AB12M4

<400> SEQUENCE: 42
gaaatcgtgc tgacccagtc tccagctaca ctggccgtgt cccctggaga gagggctacc        60
atcagctgtc gggcctctga gtctgtcgac gattacggca tctcttcat gaattggttc        120 cagcagaaac ctggccagcc ccctaaactg ctgatctatg tcgcttccaa tcagggaagc       180
ggagtgcctg ctagattcag cggatctgga tctggaaccg acttcaccct gaacatccat       240
ccaatggagg aggacgatac cgccatgtac ttctgtcagc agtctaaaga agtccctgg        300 acctttggcg gcggcacaaa gctggagatc aag                                     333
```

ANTI-PD-1 ANTIBODY AND USE THEREOF

CROSS-REFERENCE TO RELATED APPLICATIONS

This application is the United States national stage entry under 35 U.S.C. § 371 of International Application No. PCT/CN2017/092026, filed on Jul. 6, 2017 and published as WO 2018/113258 A1, which claims priority to Chinese Patent Application No. 201611198440.8, filed on Dec. 22, 2016. The contents of these applications are each incorporated herein by reference in their entirety.

FIELD

The invention relates to the field of therapeutic monoclonal antibodies and, more specifically, to an antibody targeting programmed death-1 (PD-1). The invention also relates use of the antibody in the treatment of a variety of diseases, including cancer, infectious and inflammatory diseases.

BACKGROUND

Programmed death-1 (PD-1) is a member of the CD28 family and an immunosuppressive receptor expressed on the surface of activated T cells and B cells (Yao Z et al., 2013, Nat Rev Drug Discov, 12(2):130-146), which was originally obtained from apoptotic T cell hybridomas by a subtractive hybridization technique. PD-1 is mainly expressed on the surface of CD4$^+$ T cells, CD8$^+$ T cells, NKT cells, B cells, and activated monocytes. Its expression on the surface of these cells is induced by T cell receptor (TCR) or B cell receptor (BCR) signaling and enhanced by TNF-α (Francisco LM et al., 2010, Immunol Rev, 236: 219-242). The PD-1 molecule consists of an extracellular domain, a transmembrane region, and an intracellular tail. The extracellular domain has an immunoglobulin variable region IgV domain, and the intracellular tail contains two tyrosine-based signal transduction motifs: ITIM (Immunoreceptor Tyrosine-based Inhibitory Motif) and ITSM (Immunoreceptor Tyrosine-based Switch Motif). Following activation of T cells, PD-1 recruits the tyrosine phospholipase SHP2 mainly through the ITSM motif, leading to dephosphorylation of effector molecules including CD3ζ, PKCO, and ZAP70. PD-1 has two ligands, PD-L1 and PD-L2. PD-L1 is also known as B7H1 or CD274, and PD-L2 is also called B7DC or CD273. PD-L1 and PD-L2 are expressed in different cell types (Shimauchi, Kabashima et al., 2007, Int J Cancer, 121 (12):2585-2590). In terms of expression pattern, PD-L2 expression is highly restricted, mainly in activated macrophages, dendritic cells, and a small portion of tumor cells. In contrast, PD-L1 is widely expressed on activated T cells, B cells, macrophages, dendritic cells, and tumor cells, and at sites of immune privilege, including placenta and eye, as well as vascular endothelial cells, epithelial cells, muscle cells, and hepatocytes.

PD-1 interacts with its ligands PD-L1 and PD-L2 (programmed death-1 ligands, PD-Ls) to significantly inhibit CD3/CD28-mediated T cell activation and cytokine production through intracellular signal transduction pathways, and therefore PD-1 and PD-Ls are important immune checkpoint proteins that regulates T cell responses. Under normal circumstances, the PD-1/PD-Ls signaling pathway can induce and maintain the immune tolerance of peripheral tissues, which has a positive effect on preventing excessive inflammation of tissues and the occurrence of autoimmune diseases (Latchman Y et al., 2001, Nat Immunol, 2:261-268). In a pathological state, the interaction of PD-1 with PD-L1/PD-L2 down-regulates the secretion of T-cell immunostimulatory cytokines such as IFN-γ, IL-2 and TNF-α and expression of survival proteins, and promotes the secretion of immunosuppressive cytokine IL-10, thereby inhibiting T cell immune responses (Hamid O et al., 2013, Expert Opin Biol Ther, 13(6):847-861). Studies have shown that PD-1 co-inhibitory signaling is closely related to the occurrence of various human diseases and the PD-1 co-inhibitory signaling molecules can be targeted for disease treatment (Okazaki T et al., 2007, J Immunol; 19:813-824).

The PD-1/PD-L1 signaling pathway is closely related to tumor progression. In tumor patients, PD-L1 overexpression can enhance the ability of tumor metastasis, leading to increased mortality and poor prognosis. Studies have shown that high expression of PD-L1 was detected in tumor tissues of human lung cancer, liver cancer, ovarian cancer, cervical cancer, skin cancer, bladder cancer, colon cancer, breast cancer, glioma, kidney cancer, stomach cancer, esophageal cancer, oral squamous cell carcinoma, and head and neck cancer. In addition, PD-L1 is highly expressed in tumor cells in the presence of a variety of cytokines, and associated with immune evasion of tumor cells. Meantime, tumor-infiltrating CD8$^+$ T cells at the tumor sites are also affected by the tumor microenvironment, and have higher PD-1 expression than T cells do in the peripheral blood. PD-1 interacts with PD-L1 on the surface of tumor cells, inhibiting the activation and proliferation of T cells. Tumor cells can evade the killing by cytotoxic lymphocytes (CTLs), and weaken the anti-tumor immune response of the body. Blocking PD-1/PD-L1 signaling by the anti-PD-1 monoclonal antibodies can upregulate the secretion of IFN-γ, IL-2, and IL-10, effectively reverse the proliferation inhibition of CD4$^+$ and CD8$^+$ T cells, and significantly enhance T cell activation and killability (Dong HD et al., 2002, Nat Med, 8:793-800).

Multiple chronic and acute viral infections also evade human immune surveillance through the PD-1/PD-Ls interaction. Peripheral virus-specific CD4$^+$, CD8$^+$ T cells overexpress PD-1, leading to dysfunction or incompetence in removing the infective virus promptly and effectively (Venkatachari NJ et al., 2008, Virology, 376:140-153). Recently, a large number of studies have shown that blockade of the PD-1/PD-Ls inhibitory pathway by specific monoclonal antibodies can effectively activate and proliferate HIV, HBV and HCV virus-specific CD4$^+$, CD8$^+$ T cells, produce killing factors such as IFN-γ, TNF-α and granzyme B, and restore immune cell-specific antiviral properties (Barber D L et al., 2006, Nature, 439:682-687).

Thus, specific anti-PD-1 monoclonal antibodies can be prepared to block the PD-1/PD-L1 signaling and shut down the inhibitory pathway, which will enhance the function of CTL to kill tumor cells, and effectively inhibit tumor formation and growth. Currently there are two anti-tumor anti-PD-1 antibody drugs on the market, namely Pembrolizumab (trade name Keytruda, Merck Sharp & Dohme) and Nivolumab (trade name Opdivo, Ono Pharmaceutical/Bristol-Myers Squibb). Pidilizumab, developed by Cure Tech, is in the Phase II clinical trials. AMP-224 and AMP-514, developed by MedImmune, are in the Phase I clinical trials. Although there are a variety of immune checkpoint monoclonal antibodies against PD-1, PD-L1 and CTLA4 used in clinical treatments, the response rates of these antibodies used as a single drug are still low, an average of only 15-20%. Therefore, it is necessary to develop new anti-PD-1 monoclonal antibodies with higher specificity, lower toxic side effects, and better clinical efficacy, which will provide more medication options to cancer patients and patients with infectious diseases.

SUMMARY

The object of the present invention is to provide an anti-PD-1 monoclonal antibody with high affinity for the PD-1 molecule.

One aspect of the present invention provides an isolated monoclonal antibody that binds to PD-1, which contains:
- a heavy chain variable region containing CDR-H1, CDR-H2 and CDR-H3 amino acid sequences, and
- a light chain variable region containing CDR-L1, CDR-L2 and CDR-L3 amino acid sequences, wherein:
(i) the heavy chain variable region contains a CDR-H1 sequence selected from SEQ ID NO: 1 or 2, a CDR-H2 sequence selected from SEQ ID NO: 3 or 4, and a CDR-H3 sequence selected from SEQ ID NO: 5 or 6; and
(ii) the light chain variable region contains a CDR-L1 sequence selected from SEQ ID NO: 7 or 8, a CDR-L2 sequence selected from SEQ ID NO: 9 or 10, and a CDR-L3 sequence selected from SEQ ID NO: 11 or 12.

In a preferred embodiment of the invention, the heavy chain variable region of the antibody contains the CDR-H1 sequence shown in SEQ ID NO: 1, the CDR-H2 sequence shown in SEQ ID NO: 3, and the CDR-H3 sequence shown in SEQ ID NO: 5; and the light chain variable region of the antibody contains the CDR-L1 sequence shown in SEQ ID NO: 7, the CDR-L2 sequence shown in SEQ ID NO: 9, and the CDR-L3 sequence shown in SEQ ID NO: 11.

In another preferred embodiment of the invention, the heavy chain variable region of the antibody contains the CDR-H1 sequence shown in SEQ ID NO: 2, the CDR-H2 sequence shown in SEQ ID NO: 4, and the CDR-H3 sequence shown in SEQ ID NO: 6; and the light chain variable region of the antibody contains the CDR-L1 sequence shown in SEQ ID NO: 8, the CDR-L2 sequence shown in SEQ ID NO: 10, and the CDR-L3 sequence shown in SEQ ID NO: 12.

Further, the antibodies containing the CDR sequences described above are murine, chimeric, or humanized.

For example, the antibody is murine or chimeric. Its heavy chain variable region further contains a heavy chain FR region of murine $IgG_1$, $IgG_2$, $IgG_3$, $IgG_4$, or a variant thereof; its light chain variable region contains a light chain FR region of murine κ, λ chain or a variant thereof.

More preferably, the murine or chimeric antibody contains:
(a) a heavy chain variable region comprising the amino acid sequence shown in SEQ ID NO: 15,
(b) a light chain variable region comprising the amino acid sequence shown in SEQ ID NO: 16.

For example, in preferred embodiments of the invention, the murine antibody AB12N1 and the chimeric antibody AB12N2, the heavy chain variable regions thereof comprise the amino acid sequence shown in SEQ ID NO: 15, and the light chain variable regions thereof comprise the amino acid sequence shown in SEQ ID NO: 16.

More preferably, the murine or chimeric antibody contains:
(a) a heavy chain variable region comprising the amino acid sequence of SEQ ID NO: 13;
(b) a light chain variable region comprising the amino acid sequence of SEQ ID NO: 14.

For example, in the preferred embodiments of the present invention, the murine antibody AB12M1 and the chimeric antibody AB12M2, the heavy chain variable regions thereof comprise the amino acid sequence shown in SEQ ID NO: 13, and the light chain variable regions thereof comprise the amino acid sequence shown in SEQ ID NO: 14.

For example, the antibodies are humanized Methods for preparing humanized antibodies are well known to those skilled in the art. For example, the humanized anti-PD-1 antibodies of the present invention can be prepared by transferring the CDR sequences of the invention into human antibody variable regions. The humanized antibodies do not produce anti-antibody response (AAR) or human anti-mouse antibody response (HAMA), and are not cleared rapidly due to neutralization by anti-antibodies.

In a preferred embodiment of the present invention, the murine antibody AB12M1 is humanized by CDR-grafting. In the resulting humanized antibody, preferably, the heavy chain variable region thereof comprises an amino acid sequence selected from the group consisting of SEQ ID NOs: 17, 19, 21, 23, 25, 27 and 29, and the light chain variable region thereof comprises an amino acid sequence selected from the group consisting of SEQ ID NOs: 18, 20, 22, 24, 26, 28 and 30. More preferably, in the resulting humanized antibodies AB12M3, AB12M4, AB12M5, AB12M6, AB12M7, AB12M8 and AB12M9, their heavy chain variable regions comprise the amino acid sequences of SEQ ID NOs: 17, 19, 21, 23, 25, 27 and 29, respectively, and the corresponding light chain variable regions comprise the amino acid sequences of SEQ ID NOs: 18, 20, 22, 24, 26, 28 and 30 respectively.

In another preferred embodiment of the present invention, the murine antibody AB12N1 is humanized by CDR-grafting. In the resulting humanized antibody, preferably, the heavy chain variable region comprises an amino acid sequence selected from the group consisting of SEQ ID NOs: 31, 33 and 35, and the light chain variable region comprises an amino acid sequence selected from the group consisting of SEQ ID NOs: 32, 34 and 36. More preferably, in the resulting humanized antibodies AB12N3, AB12N4 and AB12N5, the heavy chain variable regions comprise the amino acid sequences of SEQ ID NOs: 31, 33 and 35, respectively, and the corresponding light chain variable regions comprise the amino acid sequences of SEQ ID NOs: 32, 34 and 36, respectively.

Without affecting the activity of the antibody substantially, one skilled in the art is able to substitute, add and/or delete one or more (e.g., 1, 2, 3, 4, 5, 6, 7, 8, 9 or 10 or more) amino acids from the sequence of the antibody of the invention to obtain a variant of the antibody, which is to be regarded as within the scope of the present invention. For example, substitutions are for those amino acids with similar property in the variable regions. The amino acid sequences of the variants of the invention may have at least 80% sequence identity to their source amino acid sequences before modification; more preferably, the amino acid sequences of the variants of the invention may have at least 85%, 90%, 95%, 96%, 97% 98% or 99% sequence identity to their source amino acid sequences before modification.

The antibodies of the invention may be full length antibodies. For example, in some preferred embodiments, the anti-human PD-1 antibody of the invention further comprise a heavy chain constant region of human $IgG_4$ or $IgG_1$ and a human κ light chain constant region. Alternatively, the antibody may comprise only antigen-binding fragments, such as Fab or $F(ab')_2$ fragment, or single chain antibody scFv.

In any of the embodiments described above, the antibodies of the invention are able to bind to PD-1 with a $K_D$ of about 1 nM or less; in preferred embodiments, the antibodies are able to bind to PD-1 with a $K_D$ of about 100 pM or less; in more preferred embodiments, the antibodies are able to bind to PD-1 with a $K_D$ of about 10 pM or less; in the most preferred embodiments, the antibodies are able to bind to PD-1 with a $K_D$ of about 1 pM or less.

Another aspect of the present invention provides a DNA molecule encoding any one of the antibodies as described above.

For example, the DNA molecule encoding the heavy chain variable region of the preferred chimeric antibody AB12M2 of the present invention is shown in SEQ ID NO: 37, and the DNA molecule encoding the light chain variable region thereof is shown in SEQ ID NO: 38.

For another example, the DNA molecule encoding the heavy chain variable region of the preferred humanized antibody AB12M3 of the invention is shown in SEQ ID NO: 39, and the DNA molecule encoding the light chain variable region thereof is shown in SEQ ID NO: 40.

For another example, the DNA molecule encoding the heavy chain variable region of another preferred humanized antibody AB12M4 of the invention is shown in SEQ ID NO: 41, and the DNA molecule encoding the light chain variable region thereof is shown in SEQ ID NO: 42.

Another aspect of the invention provides an expression vector containing any one of the DNA molecules of the invention as described above.

Another aspect of the invention provides a host cell transfected with any one of the expression vectors as described above. Preferably the host cell is a CHO cell.

Another aspect of the invention provides an immunoconjugate comprising an antibody of the invention conjugated to a therapeutic agent. The therapeutic agent is preferably a toxin, a radioisotope, a drug, or a cytotoxic agent.

Another aspect of the invention also provides a bispecific molecule containing any one of the antibodies of the invention. For example, the above-described PD-1 antibody can be functionally linked to an antibody or antibody fragment with another antigen-binding specificity to form a bispecific antibody. For example, the bispecific antibody further comprises, but is not limited to, the antibody against the molecule such as VEGF, EGFR, HER2/neu, VEGF receptors or other growth factor receptors, CD20, CD40, CTLA-4, OX-40, 4-1BB, and ICOS.

Another aspect of the invention also provides a pharmaceutical composition containing an antibody of the invention and a pharmaceutically acceptable excipients, carriers, or diluents.

Another aspect of the invention also provides a method of preparing the antibodies of the invention, comprising: (a) culturing the above-described host cell of the invention under conditions allowing the production of the antibody, (b) recovering and isolating the antibody produced.

Another aspect of the invention also provides use of the anti-PD-1 antibodies, pharmaceutical compositions, immunoconjugates, and bispecific molecules of the invention in manufacturing a drug for the treatment of a PD-1-mediated disease or condition.

Preferably, the disease or condition is cancer, more preferably a cancer with high expression of PD-L1, and the cancer includes, but is not limited to, lung cancer, liver cancer, ovarian cancer, cervical cancer, skin cancer, bladder cancer, colon cancer, breast cancer, glioma, kidney cancer, stomach cancer, esophageal cancer, oral squamous cell carcinoma, and head and neck cancer; more preferably the cancer is breast cancer, lung cancer, stomach cancer, colon cancer, kidney cancer, or melanoma; most preferably the cancer is non-small cell lung cancer, melanoma, or kidney cancer.

Preferably, the disease is an infectious disease, for example, a chronic viral infection, bacterial infection, or parasitic infection, and more preferably the infectious disease is HIV, HBV or HCV.

In manufacturing of a drug for the treatment of cancer or infectious diseases, preferably, the chimeric or humanized anti-PD-1 antibodies may be used; more preferably, the humanized anti-PD-1 antibodies are used.

The antibodies provided by the present invention may be used alone or in combination with other therapeutic agents or therapeutic methods: for example, antineoplastic agents or immunogenic agents (e.g., tumor antigens), antigen presenting cells (e.g., dendritic cells stimulated with antigens or nucleic acids derived from tumors), immunostimulatory cytokines (e.g., IL-2, IFNA2, GM-CSF), and cells transfected with genes encoding immunostimulatory cytokines (e.g., those including but not limited to GM-CSF); standard cancer treatments (e.g., chemotherapy, radiotherapy or surgery); or other antibodies (those including but not limited to antibodies against VEGF, EGFR, HER2/neu, VEGF receptors or other growth factor receptors, CD20, CD40, CTLA-4, OX-40, 4-IBB, and ICOS).

Compared to Keytruda and Opdivo used in clinical treatments, the humanized anti-PD-1 antibodies provided by the present invention have not only a higher binding affinity for PD-1, with an affinity constant $K_D$ of less than 1 pM, but also a strong specificity. In vivo anti-tumor data have showed that the humanized antibodies provided by the present invention significantly inhibit the growth of implanted tumor in transgenic mice, and in some mice even eliminate the tumor completely. In addition, the antibodies of the present invention are expressed in CHO cells, and have the advantages of high yield, high activity, simple purification process, and low production cost.

DETAILED DESCRIPTION

Abbreviations and Definitions hPD-1, human PD-1 protein;

CDR, the complementarity-determining region of the variable region of an immunoglobulin, defined by the Kabat numbering scheme;

$EC_{50}$, the concentration of an antibody that gives half-maximal binding;

ELISA, enzyme-linked immunosorbent assay;

FR, antibody framework region, an immunoglobulin variable region that excludes the CDR regions;

HRP, horseradish peroxidase;

IL-2, interleukin 2;

IFN, interferon;

$IC_{50}$, the concentration of an inhibitor that gives 50% inhibition;

IgG, immunoglobulin G;

Kabat, an immunoglobulin numbering and alignment scheme advocated by Elvin A Kabat;

mAb, monoclonal antibody;

PCR, polymerase chain reaction;

V region, the variable sequence segment of IgG among different antibodies, which includes 1 to 109-position Kabat residues in the light chain and 1 to 113-position Kabat residues in the heavy chain;

$V_H$, the variable region of an immunoglobulin heavy chain;

$V_\kappa$, the variable region of an immunoglobulin κ light chain;

$K_D$, equilibrium dissociation constant;

$k_a$, association rate constant;

$k_d$, dissociation rate constant.

The term "antibody" as used herein includes full length antibodies (e.g., $IgG_1$ or $IgG_4$ antibodies), various functional fragments thereof (e.g., may comprise only antigen binding moieties, such as Fab, $F(ab')_2$ or scFv fragments), and modified antibodies (e.g., humanized, glycosylated, etc.). The present invention also includes anti-PD-1 antibodies with modifications by glycosylation and deglycosylation. In some applications, modifications are performed by removing undesirable glycosylation sites, such as modifications removing fucose from oligosaccharide chains to enhance the antibody-dependent cell-mediated cytotoxicity (ADCC) function; in other applications, galactosylation modification is performed to alter the antibody-mediated complement dependent cytotoxicity (CDC) activity.

The term "monoclonal antibody or mAb" refers to the antibody obtained from a single clonal strain, which is not limited to eukaryotic cells, prokaryotic cells, or phages. Monoclonal antibodies or antigen-binding fragments can be obtained using, for example, hybridoma techniques, recombinant techniques, phage display techniques, composition techniques (e.g., CDR-grafting), or several current technique combinations, etc.

The "antibody fragment" and "antigen-binding fragment" refer to the antigen-binding fragment of an antibody or an antibody analogue, which typically comprises at least a portion of an antigen-binding region or a variable region (e.g., one or more CDRs) of the parental antibody. The antibody fragment retains at least some binding specificity of the parental antibody. Typically, the antibody fragment retains at least 10% of the parent binding activity when the activity is expressed in moles. Preferably, the antibody fragment retains at least 20%, 50%, 70%, 80%, 85%, 90%, 95% or 100% or more of the binding affinity of the parental antibody to the target. Examples of antibody fragments include, but are not limited to, Fab, Fab', $F(ab')_2$, and Fv fragments; double antibodies; linear antibodies; single chain antibody molecules, e.g., scFv and UniBody (Genmab); nanobodies (Ablynx); domain antibodies (Domantis); and multispecific antibodies formed by antibody fragments. For a review on engineered antibody variants, see Holliger B et al., 2005, Nat Biotechnol, 23:1126-1136.

The "Fab fragment" consists of a light chain and the $C_H1$ region and variable region of a heavy chain. The heavy chain of the Fab molecule can not form a disulfide bond with the heavy chain of another Fab molecule.

The "Fc" region comprises two heavy chain fragments, each containing the $C_H2$ and $C_H3$ domains of an antibody. The two heavy chain fragments are held together by two or more interchain disulfide bonds and the inter-$C_H3$ domain hydrophobic interactions.

The "Fab' fragment" comprises a light chain and a heavy chain's VH domain, $C_H1$ domain, and constant region between the $C_H1$ and $C_H2$ domains, and thereby the two heavy chains of two Fab' fragments can form an interchain disulfide bond to form an F(ab')2 molecule.

The "$F(ab')_2$ fragment" comprises two light chains and two heavy chains' VH domains, $C_H1$ domains, and constant regions between the $C_H1$ and $C_H2$ domains, thereby forming an interchain disulfide bond between the two heavy chains. Thus, the $F(ab')_2$ fragment consists of two Fab' fragments that are held together by a disulfide bond between the two heavy chains.

The "Fv" region comprises the variable regions from both the heavy and light chains, but lacks constant regions.

The "single chain Fv antibody" (or "scFv antibody") refers to an antibody fragment comprising the VH and VL domains of an antibody, wherein these domains are present in a single polypeptide chain. For an scFv review, see Plückthun, 1994, The pharmacology of monoclonal antibodies, Rosenberg M and Moore G P, eds, Vol. 113, pp 269-315, Springer Verlag, New York. See also the International Patent Application Publication No. WO 88/01649 and U.S. Pat. Nos. 4,946,778 and 5,260,203.

An "antigen-binding fragment" is an immunoglobulin fragment having an immunological function that contains only a heavy chain variable region or a light chain variable region.

The term "hypervariable region" as used herein refers to the amino acid residues of an antibody responsible for antigen binding. The hypervariable region comprises the following amino acid residues: those from the "complementarity determining regions" or "CDRs", as defined by sequence alignment, residues 24-34 (L1), 50-56 (L2), and 89-97 (L3) of the light chain variable domains, and residues 31-35 (H1), 50-65 (H2), and 95-102 (H3) of the heavy chain variable domains, see Kabat E A et al., 1991, Sequences of Proteins of Immunological Interest, 5th edition, Public Health Service, National Institutes of Health, Bethesda, Md.; and/or those amino acid residues from the "hypervariable loops" (HVL), as defined by structures, residues 26-32 (L1), 50-52 (L2), and 91-96 (L3) of the light chain variable domains, and residues 26-32 (H1), 53-55 (H2), and 96-101 (H3) of the heavy chain variable domains, see Chothia C and Leskl, 1987, J MoI Biol, 196:901-917. The "framework region" (FR) residues refer to the residues in a variable region except for those in the hypervariable region defined herein.

The term "chimeric antibody" is an antibody that fuses the variable regions of a murine antibody with the constant regions of a human antibody to reduce the immune response induced by the murine antibody. For generating a chimeric antibody, it is necessary to develop hybridoma cells which secrete the specific mouse monoclonal antibody. Then the variable region genes are cloned from the mouse hybridoma cells, and the constant region genes of the human antibody are cloned as needed. The mouse variable region genes and the human constant region genes are ligated into the chimeric genes. The chimeric genes are inserted into the vectors, and finally expressed in a eukaryotic or prokaryotic expression system for production of the chimeric antibody. In a preferred embodiment of the invention, the light chain variable region of the chimeric PD-1 antibody also comprises the light chain FR regions of murine κ, λ chain or a variant thereof. The heavy chain variable region of the chimeric PD-1 antibody also comprises the heavy chain FR regions of murine $IgG_1$, $IgG_2$, $IgG_3$, $IgG_4$, or a variant thereof. The constant regions of the chimeric PD-1 antibody may be selected from the constant regions of human $IgG_1$, $IgG_2$, $IgG_3$, $IgG_4$, or a variant thereof, preferably human $IgG_2$ or $IgG_4$ constant regions, or human $IgG_1$ constant regions which have no ADCC (antibody dependent cell-mediated cytotoxicity) toxicity after amino acid mutations.

The term "bispecific molecule" means that the anti-PD-1 antibody or antigen-binding fragment thereof of the invention can be derivatized or attached to another functional molecule, such as another peptide or protein (e.g., tumor associated antigens, cytokines, and cell surface receptors) to produce a bispecific molecule that binds to at least two different binding sites or target molecules. For generating the bispecific molecule of the invention, the antibody of the invention may be functionally linked (e.g., by chemical coupling, gene fusion, non-covalent interactions or otherwise) to one or more other binding molecules, such as another antibody, antibody fragment, peptide, or binding mimetic, thereby producing the bispecific molecule. For example, the "bispecific antibody" means that two different variable domains or scFv units are bound together such that the resulting antibody recognizes two different antigens.

The term "immunobinding" or "immunobinding property" as used herein refers to non-covalent interactions that occur between the immunoglobulin molecule and the antigen that is specific for the immunoglobulin molecule. The binding strength or affinity of the immunobinding interactions can be expressed by the equilibrium dissociation constant ($K_D$) for the interactions, where the smaller the $K_D$ value, the higher the affinity. The immunobinding property of the polypeptides can be quantified using methods well known in the art. One method involves measuring the rates at which antigen-binding partner/antigen complexes are formed and dissociated. Both the "association rate constant" ($K_a$ or $K_{on}$) and "dissociation rate constant" ($K_d$ or $K_{off}$) can be calculated with the concentrations and the actual rates of association and dissociation (see Malmqvist M, 1993, Nature, 361:186-187). The ratio of $K_d/K_a$ is equal to the dissociation constant $K_D$ (see Davies et al., 1990, Annual Rev Biochem, 59:439-473). The $K_D$, $k_a$ and $k_d$ values can be measured by any effective method. In a preferred embodiment, the equilibrium dissociation constant is determined using the principles of optical interferometry (e.g., the Pall ForteBio's Octet instrument described in Example 3.4). In other preferred embodiments, the equilibrium dissociation constant may be determined using the surface plasmon resonance technique (e.g., Biacore) or a KinExA based assay. The antibody of the present invention is considered as being able to specifically bind to the PD-1 epitope, when the equilibrium dissociation constant $K_D$ is ≤10 µM, preferably ≤100 nM, more preferably ≤10 nM, and most preferably ≤100 pM to about 1 pM.

Homologous Antibodies

In yet another aspect, the heavy chain and light chain variable regions of the antibody of the invention comprise the amino acid sequences that are homologous to those of the preferred antibody described herein, while the antibody retains the desired functional properties of the anti-PD-1 antibody of the invention.

For example, the present invention provides the humanized PD-1-binding antibodies or antigen-binding fragments thereof containing a heavy chain variable region and a light chain variable region, wherein: (a) the heavy chain variable region comprises an amino acid sequence that has at least 80% amino acid sequence identity to a sequence selected from SEQ ID NOs: 17, 19, 21, 23, 25, 27, and 29; more preferably, the heavy chain variable region comprises an amino acid sequence that has at least 85%, 90%, 95%, 96%, 97%, 98%, or 99% amino acid sequence identity to a sequence selected from SEQ ID NOs 17, 19, 21, 23, 25, 27, and 29; (b) the light chain variable region comprises an amino acid sequence that has at least 80% amino acid sequence identity to a sequence selected from SEQ ID NOs: 18, 20, 22, 24, 26, 28, and 30; more preferably, the light chain variable region comprises an amino acid sequence that has at least 85%, 90%, 95%, 96%, 97%, 98%, or 99% amino acid sequence identity to a sequence selected from SEQ ID NOs: 18, 20, 22, 24, 26, 28, and 30.

Conservatively Modified Antibodies

The term "conservative modification" means that the amino acid modification does not significantly affect or alter the binding properties of the antibody containing the amino acid sequence. Such conservative modifications include amino acid substitutions, additions and deletions. Modifications can be introduced into the antibodies of the invention by standard techniques known in the art, such as site-directed mutagenesis and PCR-mediated mutagenesis. Conservative amino acid substitutions refer to the substitutions that change amino acids to different amino acids with similar side chains. The families that comprise amino acids with similar side chains have been described in detail in the art. These families include those that comprise amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine), and aromatic side chains (e.g., tyrosine, phenylalanine, tryptophan, histidine). Thus, one or more amino acid residues in the CDR regions of the antibody of the invention can be substituted with other amino acid residues from the same side chain families.

In some embodiments, an antibody of the invention contains a heavy chain variable region containing CDR-H1, CDR-H2 and CDR-H3 sequences and a light chain variable region containing CDR-L1, CDR-L2 and CDR-L3 sequences, wherein one or more of these CDR sequences contain the specific amino acid sequences based on a preferred antibody (e.g. AB12M1 or AB12N1) as described herein or their conservative modifications thereof, and the antibody retains the desired functional properties of the anti-PD-1 antibody of the invention. Therefore, the present invention provides an isolated PD-1-binding antibody or antigen-binding fragment thereof, which contains a heavy chain variable region containing CDR-H1, CDR-H2 and CDR-H3 sequences and a light chain variable region containing CDR-L1, CDR-L2, and CDR-L3 sequences, wherein: (a) the heavy chain variable region CDR-H1 sequence comprises an amino acid sequence selected from SEQ ID NO: 1 or 2 or their conservative modifications; and/or the heavy chain variable region CDR-H2 sequence comprises an amino acid sequence selected from SEQ ID NO: 3 or 4 or their conservative modifications; and/or the heavy chain variable region CDR-H3 sequence comprises an amino acid sequence selected from SEQ ID NO: 5 or 6 or their conservative modifications; and/or (b) the light chain variable region CDR-L1 sequence comprises an amino acid sequence selected from SEQ ID NO: 7 or 8 or their conservative modifications; and/or the light chain variable region CDR-L2 sequence comprises an amino acid sequence selected from SEQ ID NO: 9 or 10 or their conservative modifications; and/or the light chain variable region CDR-L3 sequence comprises an amino acid sequence selected from SEQ ID NO: 11 or 12 or their conservative modifications.

Therapeutic Uses of Anti-PD-1 Antibody

The antibodies of the invention include bispecific, polyclonal, monoclonal, and humanized antibodies, and can be used as therapeutic agents. These agents may be commonly used to treat or prevent cancer in a subject, increase vaccine efficacy, or enhance innate immune responses.

The antibody or fragment thereof of the invention that specifically binds to the PD-1 protein may be administered in the form of a pharmaceutical composition for the treatment of cancer or chronic infections.

The therapeutically effective amount of the antibody of the invention generally involves the amount required to achieve the therapeutic objective. As noted above, it is relevant to the binding interaction between the antibody and its target antigen. The amount of administration depends on not only the binding affinity of the antibody for its specific antigen but also on the pharmacokinetic properties of the antibody in the subject. In a non-limiting example, the usual effective therapeutic dose range of the antibody or antibody fragment of the invention may be from about 0.1 mg/kg body weight to about 50 mg/kg body weight. The usual frequency of administration may be, for example, from twice a day to once a week.

In the case of the use of the antibody fragments, the minimal inhibitory fragment that binds specifically to the binding domain of the target protein is preferred, for example, a fragment that is based on an antibody variable region sequence and retains the ability to bind to the target protein. Such peptides can be chemically synthesized and/or prepared by recombinant DNA techniques (see, e.g., Marasco et al., 1993, Proc Natl Acad Sci USA, 90:7889-7893). Depending on the particular indications of the treatment, the formulations may also contain more than one active compound, preferably those that do not adversely affect each other but have complementary activity. Alternatively or additionally, the composition may contain agents that enhance its function, for example, cytotoxic agents, cytokines, chemotherapeutic agents, or growth inhibitors.

Cancer

The antibody or antigen-binding fragment of the invention can be used to treat cancer, i.e., to inhibit the growth or survival of tumor cells. Preferred cancers, whose growth may be inhibited by using the antibodies of the invention, include those that are normally responsive to immunotherapy. Non-limiting examples of the preferred cancers include melanoma (e.g., malignant metastatic melanoma), kidney cancer (e.g., clear cell carcinoma), prostate cancer (e.g., hormone-resistant prostate adenocarcinoma), pancreatic adenocarcinoma, breast cancer, colon cancer, lung cancer (e.g., non-small cell lung cancer), esophageal cancer, head and neck squamous cell carcinoma, liver cancer, ovarian cancer, cervical cancer, thyroid cancer, glioblastoma, glioma, leukemia, lymphoma, and other malignancies.

Infectious Diseases

The antibodies or antibody fragments of the invention may also be used to prevent or treat infections and infectious diseases. The antibodies or antibody fragments can be used alone or in combination with vaccines to stimulate immune responses against pathogens, toxins, and autoantigens. The antibodies or antigen-binding fragments thereof can be used to stimulate immune responses to pathogenic viruses infecting human, and examples of these pathogenic viruses include, but are not limited to, HIV, hepatitis (A, B or C) virus, herpes virus (e.g., VZV, HSV-1, HAV-6, HSV-II, CMV, and Epstein-Barr virus), adenovirus, influenza virus, flavivirus, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, and arboviral encephalitis virus. The antibodies or antigen-binding fragments thereof can also be used to stimulate immune responses to infections caused by bacteria, fungi, parasites, or other pathogens.

Immune Adjuvants

The antibodies or antibody fragments of the invention may be used in combination with other recombinant proteins and/or peptides (e.g., tumor antigens or cancer cells) in order to enhance the immune responses to these proteins, i.e., used in vaccination regimens.

For example, the anti-PD-1 antibodies and their antibody fragments can be used to stimulate antigen-specific immune responses by co-administering the anti-PD-1 antibodies and target antigens (e.g., vaccines). Thus, another aspect of the present invention provides a method of enhancing the immune response of a subject to an antigen, which includes administering to a subject (i) an antigen and (ii) an anti-PD-1 antibody or its antigen-binding fragment of the invention in order to increase the immune response of the subject to the antigen. For example, the antigen may be a tumor antigen, viral antigen, bacterial antigen, or an antigen from a pathogen. Non-limiting examples of such antigens include, but are not limited to, tumor antigens, or antigens from viruses, bacteria or other pathogens.

Non-therapeutic Uses of the Antibodies and Antibody Fragments of the Invention

Non-therapeutic anti-PD-1 antibody products already exist, for example, anti-hPD-1 monoclonal antibodies J116 and J105 sold by eBioscience of San Diego, Calif., USA for flow cytometry, immunohistochemistry, and in vitro functional analysis, and anti-hPD-1 monoclonal antibody MAB1086 sold by R & D Systems of Minneapolis, Minn., USA for flow cytometry, Western blot, and ELISA. The antibodies of the invention may be used for any non-therapeutic purposes provided by current J116, J105 and/or MAB1086.

The antibodies of the present invention can be used as an affinity purification reagent.

The antibodies can also be used in diagnostic assays, for example, for the detection of PD-1 expression in specific cells, tissues or sera. For diagnostic applications, the antibodies can be labeled directly or indirectly with detectable moieties. Numerous markers can be used, which are usually classified into the following categories: biotin, fluorescent dyes, radioactive nucleotides, enzymes, iodine, and biosynthetic markers.

The antibodies of the invention can be used in any known assays, such as competitive binding assays, direct and indirect sandwich assays, and immunoprecipitation assays (Zola H, 1987, Monoclonal antibodies: a manual of techniques, pp 147-158, CRC Press, Inc.).

The antibodies can also be used in in vivo diagnostic tests. The antibodies are typically labeled with radionuclides (e.g., 111In, 99Tc, 4C, 131I, 125I, 3H, 32P, 35S, or 18F) so that the antigens or antigen-expressing cells can be localized by immunoscintigraphy or positron imaging.

Preparation of Monoclonal Antibody

The monoclonal antibodies (mAbs) of the present invention can be prepared by a variety of techniques including the conventional monoclonal antibody methodologies such as the standard somatic hybridization techniques described in Kohler G and Milstein C, 1975, Nature, 256:495. Although the somatic cell hybridization procedures are preferred, other methods of preparing monoclonal antibodies, such as virus-mediated human B cell immortalization, may also be used in principle.

The preferred animal system for the preparation of hybridomas is the murine animal system. The preparation of hybridomas using mice is a well-established procedure. The immunization protocols and the techniques for isolating immunized spleen cells for fusion are known in the art. Fusion partners such as murine myeloma cells and fusion protocols are also known.

For expression of an antibody or antibody fragment thereof, the DNA sequences encoding a portion of or full length light and heavy chains can be obtained by standard molecular biology techniques, e.g., PCR amplification or cDNA cloning using hybridoma cells expressing the target antibody, and inserted into the expression vectors such that the target genes are operatively linked to the transcriptional and translational regulatory sequences. The constructed vectors are transfected into a host cell for protein expression, and preferably the host cell is eukaryotic, more preferably a mammalian cell, such as a CHO cell and derived cell line.

The antibody can be purified by well known techniques, such as affinity chromatography using Protein A or Protein G. Subsequently or alternatively, the specific antigen or epitope thereof may be immobilized on the column to purify the immunospecific antibody by immunoaffinity chromatography. Purification of immunoglobulins has been described by Wilkinson D (The Scientist, 2000, Vol 14, No. 8, pp 25-28, published by The Scientist, Inc., Philadelphia Pa.).

The chimeric or humanized antibody of the present invention can be prepared based on the sequence of the mouse monoclonal antibody prepared as described above. The DNA sequences encoding the heavy and light chains of an immunoglobulin can be obtained from the target mouse hybridomas and engineered to include non-murine (e.g., human) immunoglobulin sequences using standard molecular biology techniques. For example, for generating a chimeric antibody, the murine variable regions can be linked to the human constant regions using methods known in the art (see, e.g., U.S. Pat. No. 4,816,567 by Cabilly et al). The isolated DNA sequence encoding the VH region can be converted to a full-length heavy chain gene by operatively linking the VH DNA sequence to another DNA sequence encoding the heavy chain constant regions ($C_H1$, $C_H2$ and $C_H3$). The sequences of the human heavy chain constant region genes are known in the art (see, e.g., Kabat E A et al., 1991, Sequences of Proteins of Immunological Interest, 5th edition, US Department of Health and Human Services, NIH Publication No. 91-3242), and DNA fragments of these constant regions can be obtained by standard PCR amplification. The heavy chain constant region may be a constant region of $IgG_1$, $IgG_2$, $IgG_3$, $IgG_4$, IgA, IgE, IgM or IgD, but most preferably an $IgG_1$ or $IgG_4$ constant region.

For generating a humanized antibody, the mouse CDR region sequences can be inserted into the human framework region sequences using methods known in the art (see U.S. Pat. No. 5,225,539 by Winter and U.S. Pat. Nos. 5,530,101; 5,585,089; 5,693,762 and 6,180,370 by Queen et al). In addition, transgenic animals may also be used for antibody humanization, for example, HuMAb mice (Medarex Inc.), which contain human immunoglobulin gene miniloci encoding unrearranged μ and γ heavy chain and κ light chain immunoglubulin sequences, together with targeted mutations that inactivate the endogenous μ and κ chain loci (see, e.g., Lonberg et al., 1994, Nature, 368:856-859); or KM mice, which carry a human heavy chain transgene and a human light chain transchromosome (see patent WO02/43478). Other methods for antibody humanization include phage display technology.

The invention will be further illustrated by the following examples, which should not be construed as further limitations on the scope of the invention. All cited drawings, references, patents, and published patent applications throughout this application are hereby expressly incorporated herein by reference.

BRIFE DESCRIPTION OF THE FIGURES

FIG. 1: Determination of the binding of AB12N1 and AB12M1 to human PD-1 by ELISA.

Figure 2A:
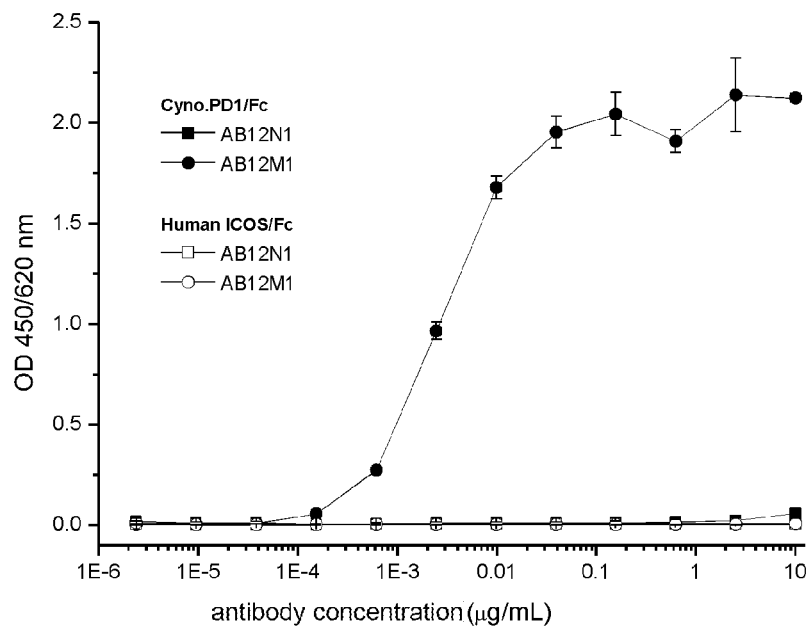

FIG. 2A: Determination of the cross-reactivity of AB12N1 and AB12M1 with cynomolgus monkey PD-1 and human ICOS by ELISA.

Figure 2B:
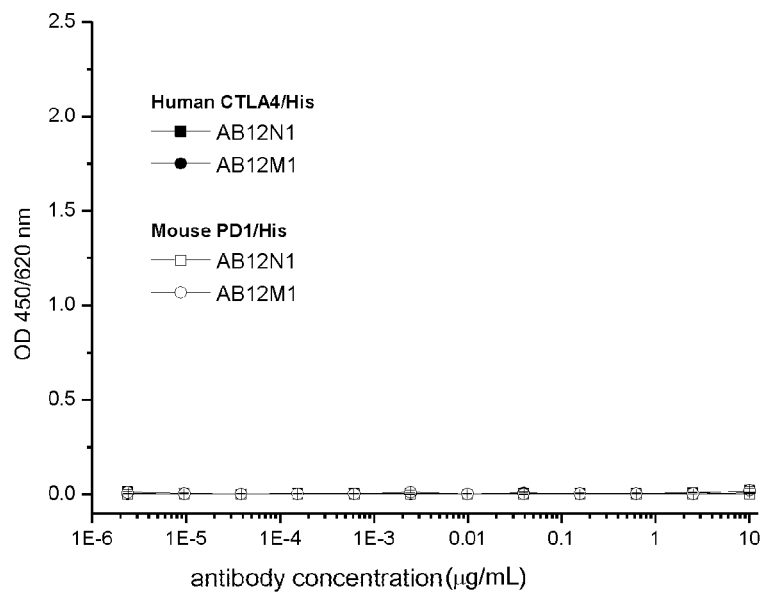

FIG. 2B: Determination of the cross-reactivity of AB12N1 and AB12M1 with human CTLA4 by ELISA.

Figure 2C:
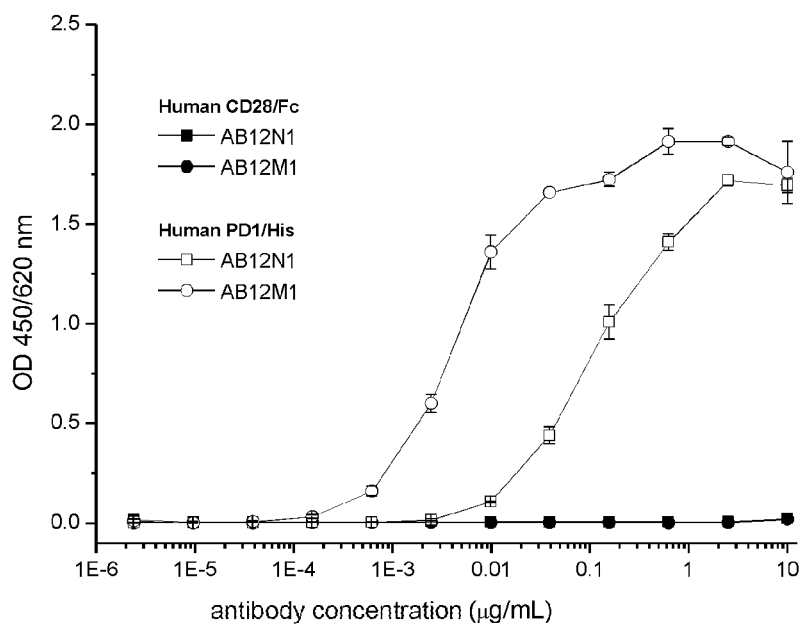

FIG. 2C: Determination of the cross-reactivity of AB12N1 and AB12M1 with human CD28 by ELISA.

Figure 3:
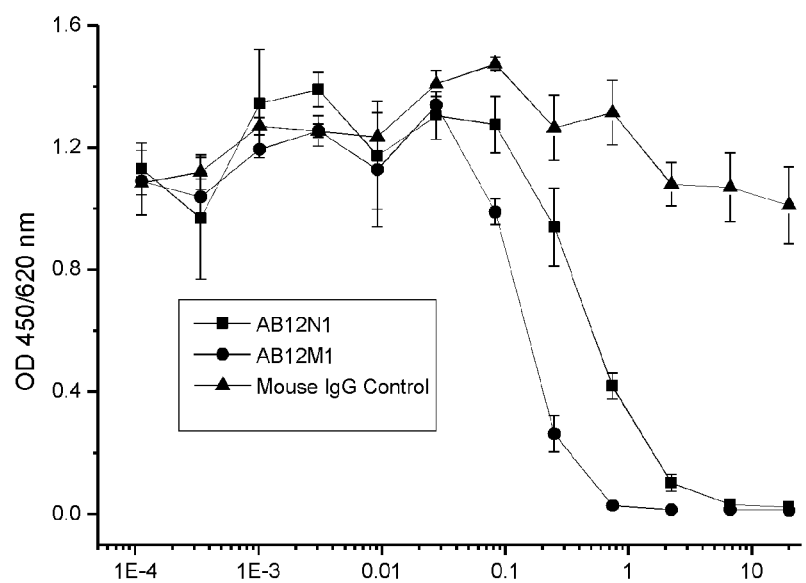

FIG. 3: Determination of the ability of AB12N1 and AB12M1 to block human PD-1/PD-L1 binding by competitive ELISA.

Figure 4:
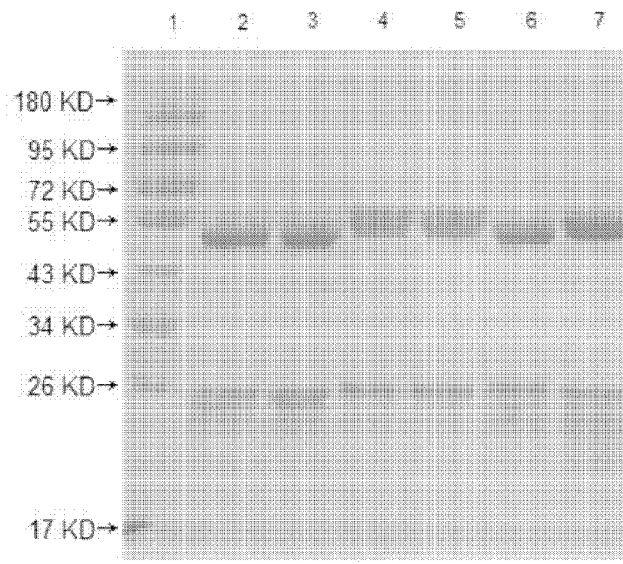

FIG. 4: Qualitative analysis of AB12N1 and AB12M1 by SDS-PAGE under reducing conditions.

Figure 5:
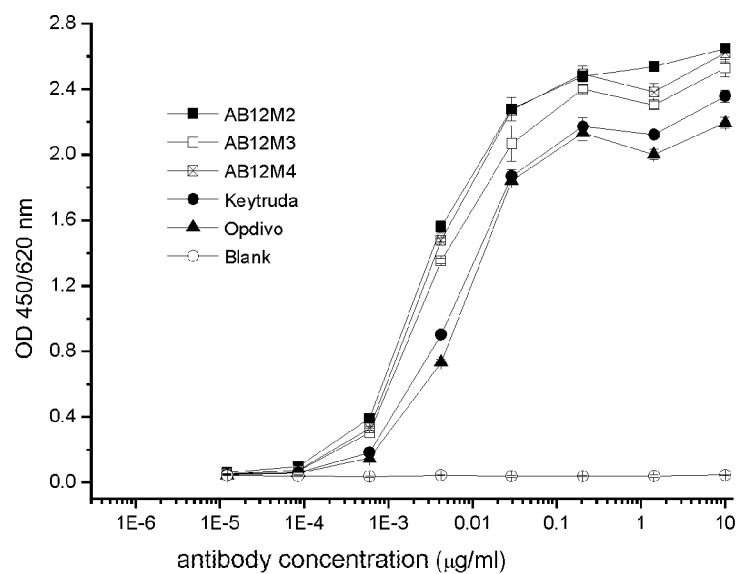

FIG. 5: Determination of the $EC_{50}$ values and specificity of AB12M2, AB12M3 and AB12M4 by ELISA.

Figure 6:
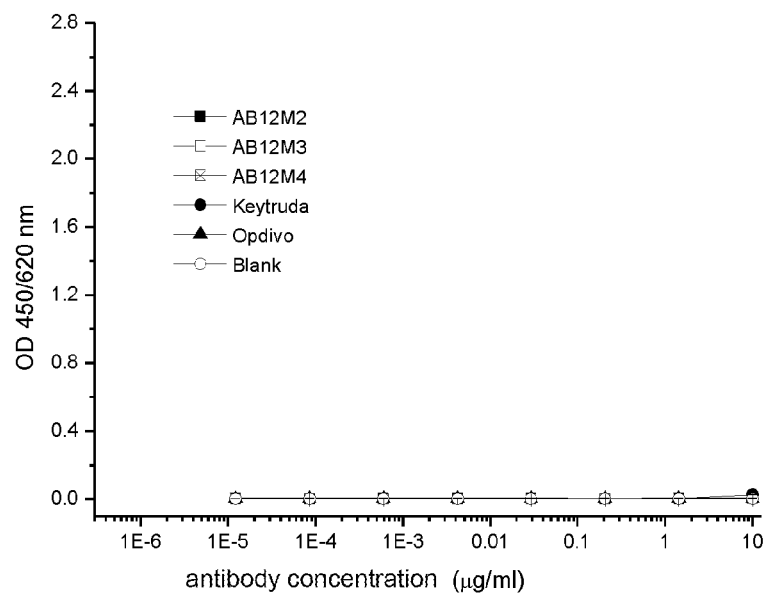

FIG. 6: Determination of the cross-reactivity of AB12M2, AB12M3 and AB12M4 with mouse PD-1 by ELISA.

Figure 7:
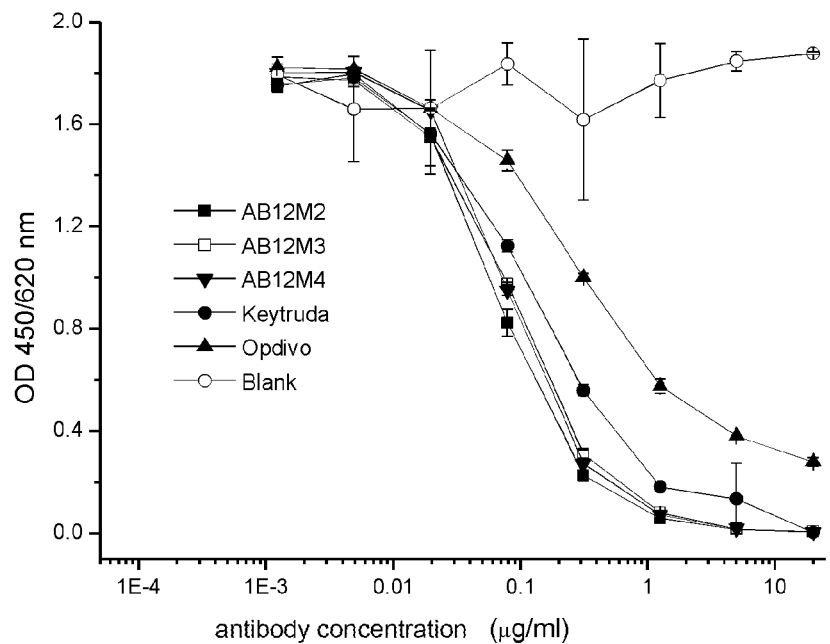

FIG. 7: Determination of the affinity of AB12M2, AB12M3, AB12M4 relative to Keytruda by competitive ELISA.

Figure 8:
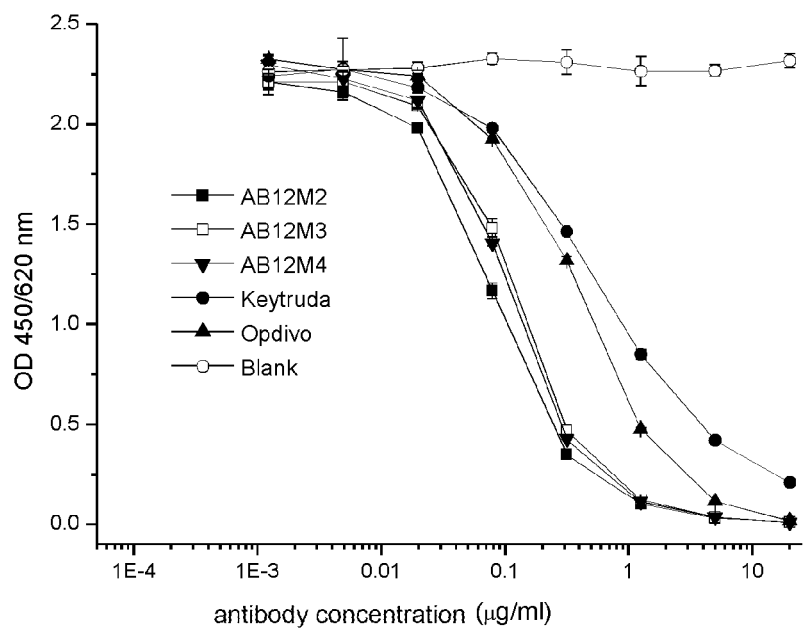

FIG. 8: Determination of the affinity of AB12M2, AB12M3, AB12M4 relative to Opdivo by competitive ELISA.

Figure 9:
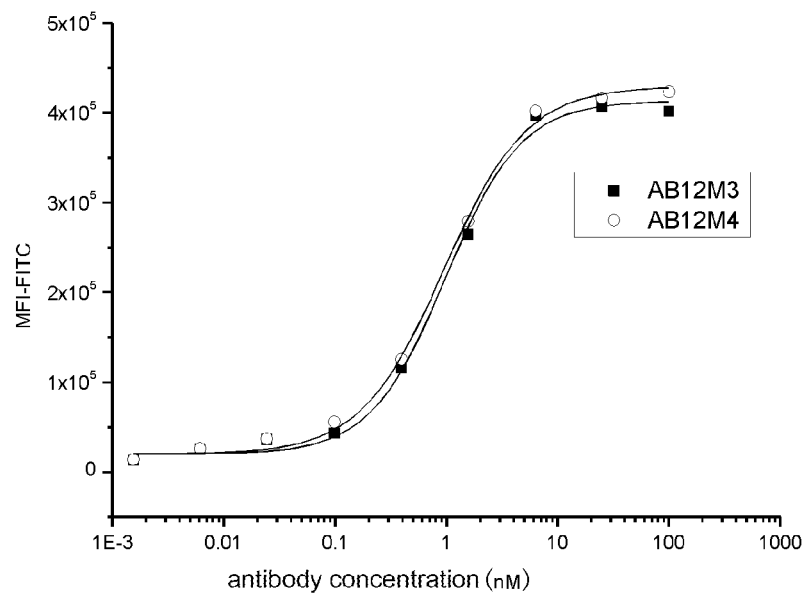

FIG. 9: AB12M3 and AB12M4 bind to PD-1-overexpressing CHO cells.

Figure 10:
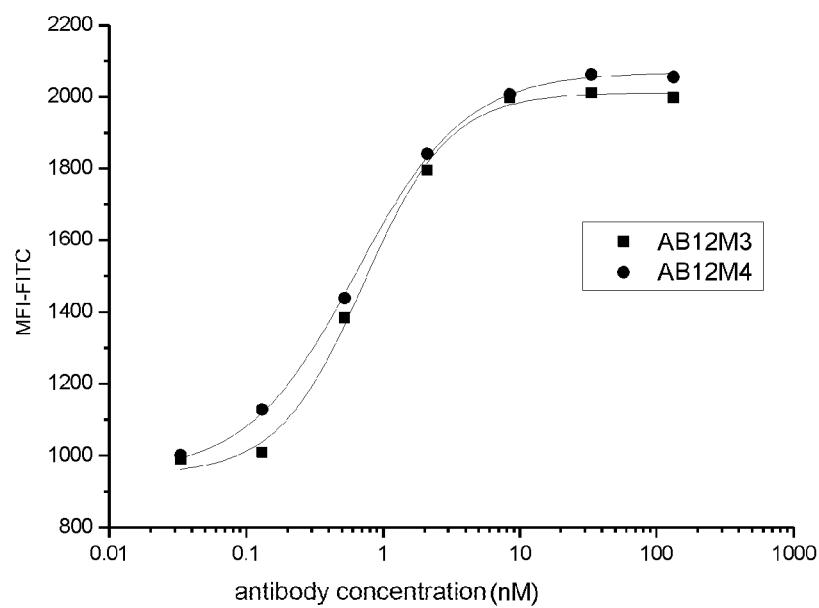

FIG. 10: AB12M3 and AB12M4 bind to activated human T cells.

Figure 11:
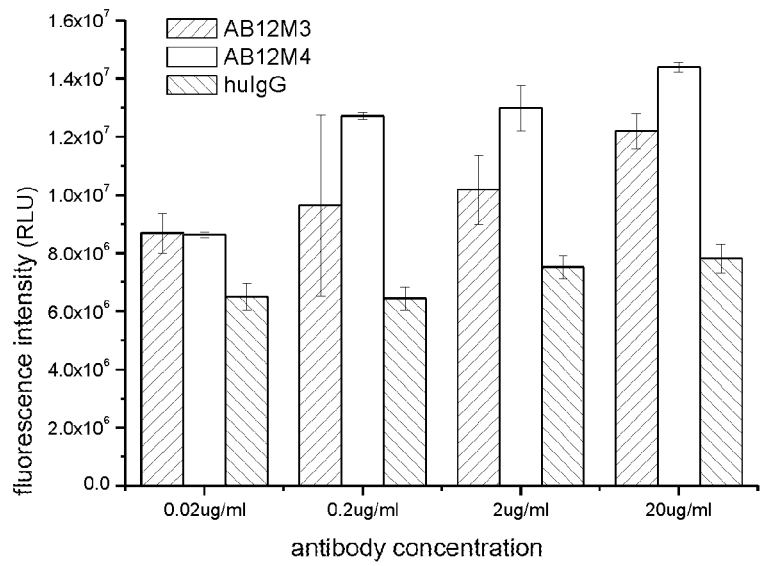

FIG. 11: AB12M3 and AB12M4 promote T cell proliferation in a concentration-dependent manner.

Figure 12:
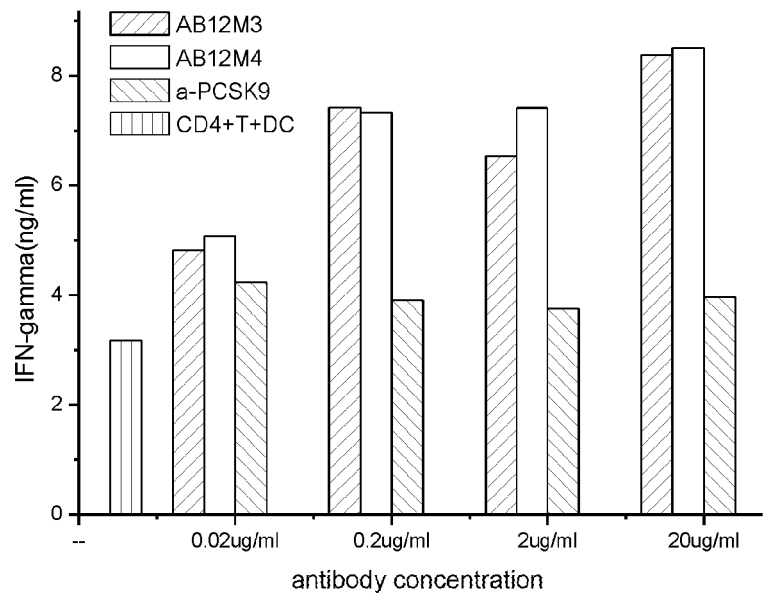

FIG. 12: AB12M3 and AB12M4 promote IFN-γ secretion in a concentration-dependent manner.

Figure 13:
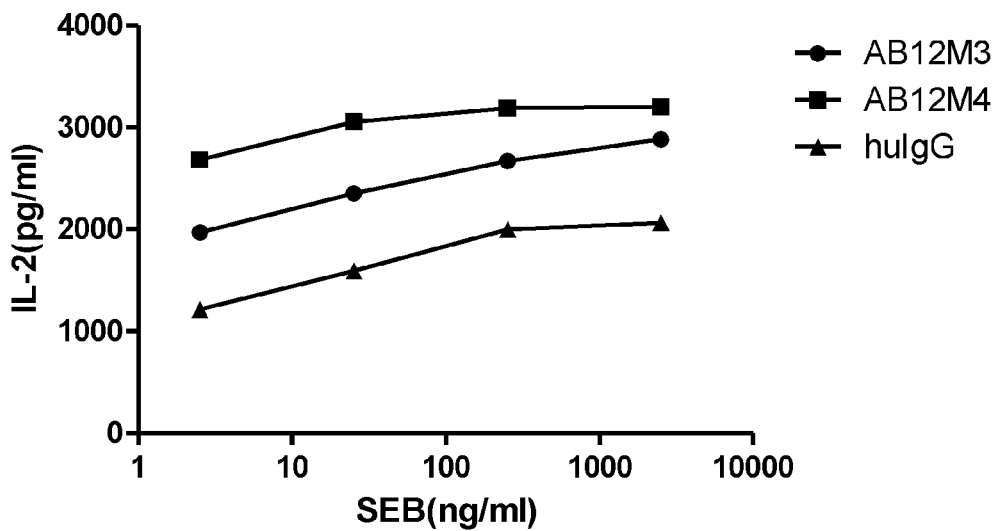

FIG. 13: AB12M3 and AB12M4 promote IL-2 secretion by T cells.

Figure 14:
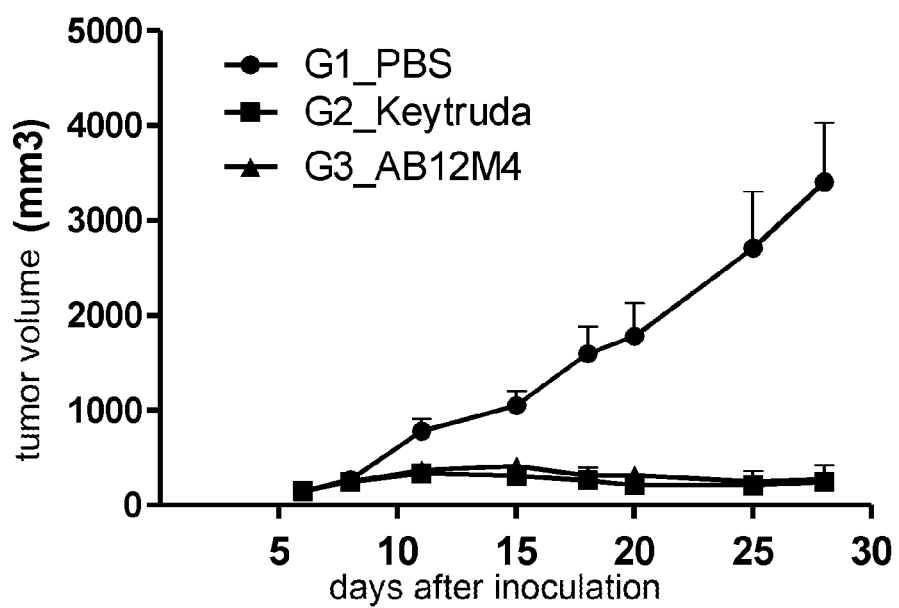

FIG. 14: AB12M4 inhibits tumor growth in mice.

EXAMPLES

Example 1

Generation of Murine Anti-Human PD-1 Monoclonal Antibodies

The male BALB/c mice were immunized at multiple sites with 50 μg of purified human PD-1 extracellular domain fragment (Sino Biological Inc., Beijing, China) emulsified with Freund's complete adjuvant. The immune cycle was once every three weeks. On the 10th day after the third immunization, blood was collected through eye socket to evaluate anti-PD-1 antibody titers in plasma by ELISA to monitor the degree of immune response in mice. The mouse with the highest anti-human PD-1 antibody titer was boosted once three days before fusion. The mouse was then sacrificed to isolate spleen cells and then fused with the Sp2/0 mouse myeloma cells. For fusion, $2\times10^8$ Sp2/0 cells were mixed with $2\times10^8$ spleen cells in a solution containing 50% polyethylene glycol (molecular weight 1450) and 5% dimethylsulfoxide (DMSO). The number of spleen cells was adjusted to $5\times10^5$/mL with Iscove's medium (containing 10% fetal bovine serum, 100 units/mL penicillin, 100 μg/mL streptomycin, 0.1 mM hypoxanthine, 0.4 μM aminopterin, and 16 µM thymidine). The 96-well culture plate with 0.3 mL of the cell suspension was placed in a 37° C., 5% $CO_2$ incubator. After 10 days of incubation, hybridoma cell culture supernatant was used to compete with the biotin-labeled human PD-L1-Fc for PD-1 binding by ELISA as in Example 3.2. Eight highly competitive positive hybridoma clones were identified. The cell clones were subcloned and murine antibodies purified from the supernatant were screened and identified again. Two positive hybridoma monoclonal cell clones #22 and #32 were obtained.

Example 2

Determination of the $EC_{50}$ Values of Murine Anti-PD-1 Antibodies by ELISA

The $EC_{50}$ values of murine monoclonal antibodies purified from the culture supernatant of the hybridoma cell strains #22 and #32 were determined by ELISA. The monoclonal antibodies secreted by the hybridoma cell strains #22 and #32 were named AB12N1 and AB12M1, respectively. Human PD-1 (Sino Biological Inc., Beijing, China) was diluted to 0.1 µg/mL with PBS buffer, and added to the 96-well plate at a volume of 100 µL/well and placed at 4° C. for 16-20 h. The PBS buffer was aspirated from the 96-well plate, and the plate was washed once with PBST (PBS containing 0.05% Tween 20, pH 7.4). 200 µL of PBST/1% no-fat milk was added to each well and incubated at room temperature for 1 h for blocking. The blocking solution was removed and the plate was washed 3 times with PBST. The murine anti-PD-1 antibody to be tested was diluted with PBST/1% no-fat milk to an appropriate concentration. 100 µL of the anti-PD-1 antibody was added to each well and incubated at room temperature for 1.5 h. The reaction solution was removed and the plate was washed 3 times with PBST. 50 µL of the HRP-labeled goat anti-mouse IgG secondary antibody (The Jackson Laboratory) diluted with PBST/1% no-fat milk (dilution ratio 1:4000) was added to each well and incubated at room temperature for 1 h. The plate was washed 3 times with PBST. 100 µL of the 3,3',5,5'-Tetramethylbenzidine (TMB) was added to each well and developed color by incubation at room temperature for 10-30 min. 50 µL of 0.2 M sulfuric acid was added to each well to terminate the reaction. The absorbance values (O.D.) were measured at dual wavelengths of 450/620 nm in a microplate reader and the $EC_{50}$ value was calculated.

As shown in FIG. 1, the murine monoclonal antibodies AB12N1 and AB12M1, expressed by the hybridoma clones #22 and #32, respectively, both were able to bind to PD-1. The $EC_{50}$ value, or antigen-binding activity, of AB12M1 was about 0.002 µg/mL, and that of AB12N1 was about 0.1 µg/mL.

Example 3

Screening and Identification of Murine Anti-PD-1 Monoclonal Antibodies 3.1. Determination of the Binding Specificity of Murine Anti-PD-1 Antibodies For determining the specific binding activities of anti-PD-1 antibodies to other proteins in the PD-1 family, human CTLA4, human CD28, and human ICOS were used for the test. Meantime, for determining the binding difference of murine anti-PD-1 antibodies to other species PD-1s other than human PD-1, PD-1s from mice and cynomolgus monkeys were used for the test.

Human PD-1/His, human ICOS/Fc, human CTLA4/His, human CD28/Fc, cynomolgus monkey PD-1/Fc, and mouse PD-1/His (all from Sino Biological Inc., Beijing, China) were diluted with PBS buffer to 0.1 µg/mL, and added to the 96-well plate at a volume of 100 µL/well and placed at 16° C. for 16 to 20 h. The PBS buffer was aspirated from the 96-well plate, and the plate was washed once with PBST (PBS containing 0.05% Tween 20, pH 7.4). 200 µL of PBST/1% no-fat milk was added to each well and incubated at room temperature for 1 h for blocking. The blocking solution was removed and the plate was washed 3 times with PBST. 100 µL of the anti-PD-1 antibody to be tested was added to each well, and incubated at room temperature for 1.5 h. The reaction solution was removed and the plate was washed 3 times with PBST. 50 µL of the HRP-labeled goat anti-mouse IgG secondary antibody (The Jackson Laboratory) diluted (dilution ratio 1:4000) was added to each well. Incubated at room temperature for 1 h. The plate was washed 3 times with PBST. 100 µL of the TMB was added to each well and incubated at room temperature for 5-10 min 50 µL of 0.2 M sulfuric acid was added to each well to terminate the reaction. Absorbance values were read at dual wavelengths of 450/620 nm in a microplate reader.

As shown in FIG. 2A, FIG. 2B, and FIG. 2C, AB12N1 and AB12M1 had no specific binding to the other three proteins of the PD-1 family. Meantime, AB12N1 and AB12M1 did not cross-react with mouse PD-1, but AB12M1 specifically bound to cynomolgus monkey PD-1, which AB did not bind to.

3.2. Murine Anti-PD-1 Antibodies Block the Binding of PD-1 to PD-L1

The biotin-labeled human PD-L1 was used as a reagent. Human PD-1 (Sino Biological Inc., Beijing, China) was diluted to 2.0 µg/mL with PBS buffer, added to the 96-well plate at a volume of 100 µL/well, and allowed to stand overnight at room temperature. The coating solution was removed, 200 µL of PBST/1% no-fat milk was added to each well, and incubated at room temperature for 1 h. The blocking solution was removed and the plate was washed 3 times with PBST. Then a mixture of 50 µL of the diluted murine monoclonal antibody AB12N1 or AB12M1 and 50 µL of the biotin-labeled human PD-L1 was added to each well, and incubated thoroughly. Unbound antibody and biotin-labeled PD-L1 were washed away with PBST. Then 100 µL of the HRP-labeled avidin was added to each well. After thorough incubation, unbound HRP-labeled avidin was washed away with PBST. 100 µL of the TMB substrate solution was added to each well and developed color for 30 min. The reaction was quenched with 0.2 M sulfuric acid and the absorbance values were read at dual wavelengths of 450/620 nm using a microplate reader. As shown in FIG. 3, the murine antibodies AB12N1 and AB12M1 specifically blocked the binding of PD-1 to PD-L1, and AB12M1 was significantly better than AB12N1 in blocking the binding of PD-1 to PD-L1.

3.3. SDS-PAGE Analysis and Western Blot Identification of Purified Murine Anti-PD-1 Antibodies The purified murine monoclonal antibodies AB12N1 and AB12M1 were qualitatively and semi-quantitatively analyzed by SDS-PAGE electrophoresis and immunoblotting (Western blotting). A 12% SDS-PAGE gel was prepared according to the recipe, and 4 µg of antibodies AB12N1, AB12M1, Keytruda, and Opdivo were loaded to each lane, respectively. Running the gel until the dye reached the bottom of the resolving gel. The power was disconnected. The electrophoresis results were observed using a gel imaging system. As shown in FIG. 4, under reducing conditions, the SDS-PAGE gel showed clear and homogeneous two bands for both of the murine antibodies AB12N1 and AB12M1, with one being the heavy chain of about 50 kD and the other the light chain of about 25 kD, respectively. Lanes were loaded as follows: lane 1, markers; lane 2, AB12N1; lane 3, AB12N1; lane 4, AB12M1; lane 5, AB12M1; lane 6, Keytruda; and lane 7, Opdivo.

According to the SDS-PAGE gel-making recipe, a 15% non-reducing SDS-PAGE gel was prepared. 5 μg of human PD-1 sample was loaded onto the gel. Running the gel until the dye reached the bottom of the resolving gel. The power was disconnected. The gel was removed and laid flat on a same-sized nitrocellulose membrane. According to the gel area, a power at 1 mA/cm$^2$ was supplied, and electrically transferred for 2 to 4 h. The membrane was immersed in the blocking solution and incubated at 4° C. overnight. The membrane was washed 3 times with PBST, each time of 10 min. Then excess AB12N1 or AB12M1 antibody was added and incubated for 1 h. The membrane was washed 3 times with PBST, each time of 10 min, and then incubated for 1 h with the HRP-goat anti-mouse IgG Fc secondary antibody diluted at 1:5000. The membrane was washed 3 times with PBST buffer. Developing color without light in the DAB substrate solution for 15 min Followed by rinsing with water to terminate the reaction immediately after bands appeared. Taking pictures for qualitative and quantitative analysis.

The Western blot results showed a PD-1 target band of about 34 kD, indicating that both AB12N1 and AB12M1 specifically bound to human PD-1.

3.4. Kinetic Analysis and Affinity Determination of Murine Anti-PD-1 Antibodies

We used the bio-layer interferometry (BLI) technique to characterize the binding kinetics and affinity of purified murine monoclonal antibodies. According to the standard procedure, the Octet molecular interaction instrument (ForteBio Octet RED & QK system, PALL corp.) was operated. The antibodies Keytruda and Opidivo were used as controls. For the multi-channel parallel quantitative analysis, the concentration gradients of antibodies were set at 3.125, 6.25, 12.5, 25, 50, and 100 nM, and human PD-1/His (Sino Biological Inc., Beijing, China) was coupled to the Ni-NTA sensor. The antigen-antibody association and dissociation kinetics were then tracked. The data were analyzed to produce the $k_a$ ($k_{on}$), $k_d$ ($k_{off}$), and $K_D$ values, which were shown in Table 1. The equilibrium dissociation constant $K_D$ between the murine monoclonal antibody AB12M1 and human PD-1 was <1.00×10$^{-12}$ M, which was comparable to those of the control antibodies Keytruda and Opidivo. Meantime, the $K_D$ value of AB12N1 was 3.51×10$^{-10}$ M, indicating that its binding affinity was lower than those of the control antibodies Keytruda and Opidivo.

TABLE 1

Determination of affinity constants of murine monoclonal antibodies AB12M1 and AB12N1

| antibody | $K_D$ (M) | $K_a$ (M/s) | $K_d$ (1/s) |
|---|---|---|---|
| AB12M1 | <1.00E−12 | 1.09E+05 | <1.00E−07 |
| AB12N1 | 3.51E−10 | 6.92E+04 | 2.08E−05 |
| Keytruda | 2.05E−12 | 2.48E+05 | 5.08E−07 |
| Opdivo | 5.60E−12 | 1.92E+05 | 1.07E−06 |

Example 4

Subclass Identification and Variable Region Amplification of Murine Anti-PD-1 Monoclonal Antibodies Antibody subclass identification: Using the IsoStrip™ mouse monoclonal antibody isotyping kit (Santa Cruz Biotechnology, Cat. No. sc-24958), the hybridoma cell culture supernatant was taken to identify the antibody subclass. The subclass of the monoclonal antibody AB12N1 was identified as IgG$_1$ (Kappa) and the subclass of the monoclonal antibody AB12M1 was IgG$_{2b}$ (Kappa).

Antibody variable region amplification: The candidate hybridoma cells #22 or #32 were cultured to a total of 10$^7$ cells, and the cells were collected by centrifugation at 1000 rpm for 10 min. The total RNA was extracted using the TRIzol kit (Invitrogen). The first-strand cDNA was generated using the SMARTer RACE reverse transcription kit (Clontech). Using the first-strand cDNA as a template, the variable region DNA sequence of the monoclonal antibody secreted by the hybridoma cells was to be amplified after designing the primers. Based on the subclass identification results, the heavy and light chain constant region sequences of the antibody subclass were known, and specific nested PCR primers were designed according to the sequences. The primer sequences used in the amplification reaction were complementary with the nucleotide sequence of the 1st framework region of the variable region and that of the constant region of the antibody. The target genes were amplified by the conventional PCR method and amplified products were sequenced. For antibody AB12N1 secreted by the hybridoma clone #22, the heavy chain variable region sequence was SEQ ID NO: 15 and the light chain variable region sequence was SEQ ID NO: 16. The amino acid sequences of the heavy chain CDRs (CDR-H1, CDR-H2 and CDR-H3) of the antibody were shown in SEQ ID NOs: 2, 4 and 6, respectively, and those of the light chain CDRs (CDR-L1, CDR-L2 and CDR-L3) were shown in SEQ ID NOs: 8, 10 and 12, respectively. For antibody AB12M1 secreted by the hybridoma clone #32, the heavy chain variable region sequence was SEQ ID NO: 13 and the light chain variable region sequence was SEQ ID NO: 14. The amino acid sequences of the heavy chain CDRs (CDR-H1, CDR-H2 and CDR-H3) of the antibody were shown in SEQ ID NOs: 1, 3 and 5, respectively, and those of the light chain CDRs (CDR-L1, CDR-L2 and CDR-L3) were shown in SEQ ID NOs: 7, 9 and 11, respectively.

Example 5

Humanization of Murine Anti-PD-1 Antibodies

Based on the variable region sequences of the AB12N1 and AB12M1 antibodies obtained above, antibody humanization was carried out using computer-aided three-dimensional modeling and structural analysis of the antibodies. CDR-grafting is a common antibody humanization method, which retains activity while reducing the immunogenicity of the murine antibody by replacing FR residues of the human antibody with murine FR residues. The antibody humanization method that utilized the Discovery Studio analysis tool for CDR-grafting mainly included the following steps: (1) Modeling of the three-dimensional structure of the antibody (2) Key residue analysis. The amino acid sequences of the variable regions and their surrounding framework residues were analyzed by molecular docking, and the spatial steric binding ways were investigated to identify the key residues critical to maintaining the conformations of the CDR regions. There were mainly three kinds of key residues: first, those located on the binding interface between the $V_L$ and $V_H$ regions, which played a key role in the folding of the two domains; second, those near the CDR regions and buried in the protein; third, those that interacted directly with the CDR regions through hydrophobic interactions, hydrogen bonds, and salt bridges. (3) Human antibody template selection. The selection process included the following two steps. First, the amino acid sequence of the antibody secreted by each hybridoma cell strain was aligned with the amino acid sequences of human germline antibodies to find the highly homologous human sequences. Second, for reducing immunogenicity, the framework region sequences of human germline antibodies with low binding affinity for HLA-DR of MHC II were chosen. And (4) based on the analysis of the key residues, grafting from the murine antibody to the human germline antibody was carried out to obtain a humanized antibody sequence.

By using the human heavy chain variable region sequence $V_H3$-23 and the human light chain variable region sequence $V_K3D$-11 as the templates, 7 humanized antibodies were obtained from the murine antibody AB12M1, which were AB12M3, AB12M4, AB12M5, AB12M6, AB12M7, AB12M8, and AB12M9. Meantime, a mouse-human chimeric antibody AB12M2 was constructed. The heavy chain variable region of the murine antibody was grafted onto the human IgG$_1$ heavy chain constant region, and the light chain variable region of the murine antibody was grafted onto the human Kappa light chain constant region. The variable region amino acid sequences of the humanized antibodies described above were shown in Table 2 below.

By using the human heavy chain variable region sequence $V_H3$-33 and the human light chain variable region sequence $V_K3$-11 as the templates, 3 humanized antibodies were obtained from the murine antibody AB12N1, which were AB12N3, AB12N4, and AB12N5. Meantime, a mouse-human chimeric antibody AB12N2 was constructed. The heavy chain variable region of the murine antibody was grafted onto the human IgG$_1$ heavy chain constant region, and the light chain variable region of the murine antibody was grafted onto the human Kappa light chain constant region. The variable region amino acid sequences of the humanized antibodies described above were shown in Table 2 below.

The humanized antibodies AB12M3, AB12M4, AB12M5, AB12M6, AB12M7, AB12M8 and AB12M9 contained more than 95% human sequences. Their affinity and kinetic constants were listed in Table 3. According to Table 3, the humanized antibodies almost all had a $K_D$ value below $1 \times 10^{-12}$ M, and did not have significant loss of the binding affinities compared to the murine antibody AB12M1 and the chimeric antibody AB12M2. Therefore the humanized antibodies retained the affinity and specificity of the parent mouse monoclonal antibody and greatly reduced the immunogenicity.

Another group of humanized antibodies AB12N3, AB12N4, and AB12N5 also contained more than 95% human sequences, and the $K_D$ values were on the order of $10^{-10}$ M, indicating that the humanized antibodies did not show significant loss of the binding affinities compared to the murine antibody AB12N1 and the chimeric antibody AB12N2.

TABLE 2

Variable region amino acid sequences of humanized antibodies

| antibody | VH sequence | VL sequence |
|---|---|---|
| AB12M3 | SEQ ID NO: 17 | SEQ ID NO: 18 |
| AB12M4 | SEQ ID NO: 19 | SEQ ID NO: 20 |
| AB12M5 | SEQ ID NO: 21 | SEQ ID NO: 22 |
| AB12M6 | SEQ ID NO: 23 | SEQ ID NO: 24 |
| AB12M7 | SEQ ID NO: 25 | SEQ ID NO: 26 |
| AB12M8 | SEQ ID NO: 27 | SEQ ID NO: 28 |
| AB12M9 | SEQ ID NO: 29 | SEQ ID NO: 30 |
| AB12N3 | SEQ ID NO: 31 | SEQ ID NO: 32 |
| AB12N4 | SEQ ID NO: 33 | SEQ ID NO: 34 |
| AB12N5 | SEQ ID NO: 35 | SEQ ID NO: 36 |

TABLE 3

Affinity comparision of humanized antibodies

| antibody | $K_D$ (M) | $K_a$ (1/Ms) | $K_d$ (1/s) |
|---|---|---|---|
| AB12M2 | <1.0E-12 | 1.98E+05 | <1.0E-07 |
| AB12M3 | <1.0E-12 | 2.26E+05 | <1.0E-07 |
| AB12M4 | <1.0E-12 | 2.13E+05 | <1.0E-07 |
| AB12M5 | <1.0E-12 | 1.69E+05 | <1.0E-07 |
| AB12M6 | <1.0E-12 | 1.99E+05 | <1.0E-07 |
| AB12M7 | 2.42E-12 | 2.41E+05 | 5.84E-07 |
| AB12M8 | <1.0E-12 | 1.84E+05 | <1.0E-07 |
| AB12M9 | 4.11E-12 | 1.48E+05 | 6.08E-07 |
| AB12N2 | 3.59E-10 | 6.58E+04 | 2.36E-05 |
| AB12N3 | 3.65E-10 | 6.24E+04 | 2.28E-05 |
| AB12N4 | 3.78E-10 | 6.37E+04 | 2.41E-05 |
| AB12N5 | 4.14E-10 | 6.19E+04 | 2.56E-05 |

Example 6

Functional Characterization of Humanized Anti-PD-1 Antibodies 6.1. Determination of the EC$_{50}$ Values and Binding Specificity of Humanized Antibodies by Indirect ELISA The EC$_{50}$ values of the humanized antibodies AB12M3 and AB12M4 and the chimeric antibody AB12M2 to antigen PD-1 were determined by indirect ELISA. Keytruda and Opdivo were used as control antibodies and medium as negative control. The HRP-labeled goat anti-human IgG antibody (The Jackson Laboratory) was used as the secondary antibody, and the detailed assay procedure was as described in Example 2. The same assay was used to detect the presence or absence of the cross reactions of the humanized antibodies AB12M3 and AB12M4 and the chimeric antibody AB12M2 with mouse PD-1 (Sino Biological Inc., Beijing, China), also using Keytruda and Opdivo as control antibodies and medium as negative control.

As shown in FIG. 5, the humanized antibodies AB12M3 and AB12M4 and the chimeric antibody AB12M2 all were able to specifically bind human PD-1, and their antigen-binding activities, the EC$_{50}$ values, were between about 0.001-0.01 µg/mL, lower than those of the control antibodies Keytruda and Opdivo. This indicated that the humanized anti-PD-1 antibodies AB12M3 and AB12M4 and the chimeric antibody AB12M2 constructed by the present invention did not show reduction of the PD-1-binding ability due to humanization, and the high affinity of the parent mouse antibody was retained. Furthermore, they did not bind to mouse PD-1, indicating the strong species binding specificity (FIG. 6).

6.2. Determination of the Relative Affinity of Humanized Anti-PD-1 Antibodies Keytruda and Opdivo labeled with horseradish peroxidase (HRP) were used as reagents. Human PD-1 (Sino Biological Inc., Beijing, China) was diluted to 0.1 µg/mL with PBS buffer and added to the 96-well plate at a volume of 100 µL/well and allowed to stand overnight at room temperature. The coating solution was removed, 200 µL of PBST/1% no-fat milk was added to each well and incubated at room temperature for 1 h for blocking. The blocking solution was removed and the plate was washed 3 times with PBST. Then the mixture of 50 µL of growth medium (DMEM+5% PBS) and 50 µL of the HRP-labeled Keytruda or Opdivo was added. Unbound HRP-labeled Keytruda or Opdivo was washed away. Antibody AB12M2, AB12M3, or AB12M4 was then added, and unlabeled Keytruda or Opdivo was used as positive control, After thorough incubation, unbound HRP-labeled Keytruda or Opdivo was washed away with PBS and the absorbance values were read at dual wavelengths of 450/620 nm using a microplate reader.

Results were shown in FIGS. 7 and 8. Antibodies AB12M2, AB12M3 and AB12M4 remarkably competitively blocked the binding of Keytruda or Opdivo to PD-1, and the $EC_{50}$ values of AB12M2, AB12M3 and AB12M4 that competed with Keytruda-HRP or Opdivo-HRP for binding to PD-1 were lower than that of Keytruda or Opdivo, all between 0.1 and 1 µg/mL. Therefore, it could be concluded that the affinities of antibodies AB12M2, AB12M3 and AB12M4 were comparable to those of Keytruda and Opdivo.

6.3. In Vitro Blockade of PD-1/PD-L1 Binding by Humanized Anti-PD-1 Antibodies The extracellular domain fragment of PD-1 protein containing His tag was coated onto the 96-well ELISA plate. After blocking and washing, the anti-PD-1 antibody to be tested was added, and meantime the biotin-labeled PD-L1-Fc was added and incubated. After washing the plate, the amount of bound biotin-labeled PD-L1-Fc was measured and the $IC_{50}$ value of the PD-1 antibody that blocked the binding of PD-1 to its ligand PD-L1 was calculated.

PD-1/His was diluted to 2 µg/mL with PBS buffer, pH 7.2, and added to the 96 well ELISA plate at 100 µL per well and incubated with shaking at room temperature for 1 h. The PBS buffer was aspirated from the 96-well ELISA plate. 200 µL of PBST(PBS containing 0.05% Tween 20, pH 7.4)/1% no-fat milk was added to each well and incubated at room temperature for 1 h for blocking. The plate was washed 3 times with PBST. 50 µL of the anti-PD-1 antibody to be tested was added to each well, which was diluted with the blocking solution to an appropriate concentration. Meantime, 50 µL of the biotin-labeled PD-L1/Fc diluted to 200 ng/mL with the blocking solution was added to each well. Incubating at room temperature for 1 h. The plate was washed 3 times with PBST. 100 µL of SA-Avidin-HRP (HRP-labeled streptavidin) diluted at 1:250 ratio with the blocking solution was added to each well, and incubated at room temperature for 1 h. Washing the plate 3 times with PBST. 100 µL of the TMB substrate solution was added to each well and incubated at room temperature for 5-10 min. Adding 50 µL of 0.2 M sulfuric acid to each well to terminate the reaction. The absorbance values were read at 450 nm in a microplate reader. The $IC_{50}$ value of the anti-PD-1 antibody that blocked the binding of PD-1 to its ligand PD-L1 was calculated.

As the experimental results in Table 4 showed, antibodies AB12M3 and AB12M4 both were effective in blocking the binding of PD-1 to PD-L1 and were superior to Keytruda and similar to Opdivo.

TABLE 4

The $IC_{50}$ values of antibodies AB12M3 and AB12M4 during in vitro blockade of PD-1/PD-L1 binding

| antibody | AB12M3 | AB12M4 | Keytruda | Opdivo |
|---|---|---|---|---|
| $IC_{50}$ (pM) | 114.3 | 96 | 126.5 | 96 |

6.4. In Vitro Cell Binding Activity of Humanized Anti-PD-1 Antibodies

FACS (fluorescence activated cell sorting) is a test used for detection of the binding between proteins and cells. The test was used to detect the binding activity of the humanized anti-PD-1 antibodies of the present invention to native PD-1 expressed on the cell surface. The cells used in the test were PD-1-overexpressing CHO cells. $3 \times 10^5$ CHO cells were incubated with the test antibody AB12M3 or AB12M4 (primary antibody) in a series of gradient concentrations for 30 min After washing, the FITC-labeled goat anti-human IgG secondary antibody (BD Biosciences) was added and incubated for 30 min. The FITC signals were detected by flow cytometry. The results in FIG. 9 showed that AB12M3 and AB12M4 could specifically bind to PD-1 overexpressed on the surface of CHO cells.

6.5. Test of the Specific Binding Between Humanized Anti-PD-1 Antibodies and Activated Human T Cells Fresh mononuclear cells were obtained from human peripheral blood by density gradient centrifugation (Lymphoprep™, human lymphocyte separation solution, STEMCELL), and high purity T lymphocytes were obtained using T cell isolation reagents (STEMCELL). The T lymphocytes were stimulated with 5 µg/mL of the anti-CD3 antibody for 48 h, and cultured for 7 days after addition of 250 IU/mL of human IL-2. A large number of activated T lymphocytes were then obtained. $3 \times 10^5$ activated T lymphocytes were incubated with the test antibody AB12M3 or AB12M4 (primary antibody) in a series of concentration gradients for 30 min After washing, the FITC-labeled goat anti-human IgG secondary antibody (BD Biosciences) was added and incubated for 30 min. The FITC signals were detected by flow cytometry. The results in FIG. 10 showed that AB12M3 and AB12M4 could specifically bind to PD-1 expressed on the surface of activated T cells.

Example 7

Determination of the Biological Activities of Humanized Anti-Human PD-1 Antibodies

7.1. Effects of Humanized Anti-PD-1 Antibodies on Cell Proliferation and Cytokine Secretion in the Mixed Lymphocyte Reaction The mixed lymphocyte reaction was used to demonstrate the effects of blocking the PD-1/PD-L1 pathway on lymphoid effector cells. The effects of anti-PD-1 antibodies and the IgG isotype control antibody on T cell proliferation and IFN-γ secretion in the mixed lymphocyte reaction were determined.

Freshly isolated human peripheral blood mononuclear cells (PBMCs) were adjusted to a cell density of $2.0 \times 10^6$ cells/mL, and monocytes were obtained by the adherent method. 100 ng/mL GM-CSF and 100 ng/mL IL-4 were added and cultured for 5 days. Then 100 ng/mL TNF-α was added to induce DC cell maturation. CD4+ T cells were isolated from fresh human PBMCs using the human CD4 positive selection kit (STEMCELL). In the 96-well plate, each well contained 250 μL of culture medium containing $10^5$ isolated T cells, $10^4$ mature DC cells, and a series of concentration gradients of AB12M3 or AB12M4. The IgG isotype control antibody was used as negative control. The mixed T and DC cells were cultured in a 37° C., 5% $CO_2$ incubator for 6 days, and then 100 μL of culture supernatant was removed from each well of the 96-well plate for determination of IFN-γ concentration. The IFN-γ concentration was determined using an OptEIA ELISA kit (BD Biosciences). The number of viable cells in the 96-well plate was determined using the CellTiter-Glo kit (Promega) to measure cell proliferation. The results showed that AB12M3 and AB12M4 promoted T cell proliferation (FIG. 11) and IFN-γ secretion (FIG. 12) in a concentration-dependent manner.

7.2. Effects of Humanized Anti-PD-1 Antibodies on Cytokine Secretion of Human PMBCs Induced by Superantigen Stimulation Freshly isolated human PBMC cells were resuspended into $10^6$ cells/mL with the RPMI 1640 medium containing 10% inactivated FBS and 20 μg/mL AB12M3 or AB12M4 or the IgG isotype control antibody, and inoculated into the 96-well plate, 100 μL/well. The highest concentration of superantigen SEB was 2500 ng/mL, which was diluted in 4 serial 10-fold dilutions and added to the 96-well plate in triplet. The cells were cultured for 72 h. The supernatant was taken to determine the IL-2 concentration using the OptEIA ELISA kit (BD Biosciences). The results in FIG. 13 showed that AB12M3 and AB12M4 could promote IL-2 secretion by T cells.

7.3. In vitro tumor cell killing effects of stimulating T cells by humanized anti-PD-1 antibodies The human non-small cell lung cancer cell line HCC827 that overexpressed PD-L1 (The Cell Bank of Chinese Academy of Sciences (Shanghai)) was inoculated into the 96-well cell culture plate. A series of concentrations of AB12M1, AB12M3, AB12M4 or huIgG were added. Then the T cells that were activated by both the anti-CD3 antibody and IL-2 were added at a 10:1 effector/target ratio and cultured for 48 h. The plate was washed with medium to remove most of the T cells. The viability of the HCC827 cells was analyzed using the CCK-8 cell proliferation kit (Dojindo), and the killing rate was calculated. The results in Table 5 showed that AB12M3 and AB12M4 had the ability to enhance T cells' killing of the tumor cells.

TABLE 5

The killing rates of the humanized antibodies
AB12M3 and AB12M4 on tumor cells (%)

| dose (μg/mL) | AB12M1 | AB12M3 | AB12M4 | huIgG |
|---|---|---|---|---|
| 100 | 58.2 | 30.3 | 59.1 | 21.8 |
| 10 | 37.3 | 22.0 | 32.9 | 30.8 |
| 1 | 30.2 | 23.5 | 21.9 | 20.0 |
| 0.1 | 28.8 | 20.0 | 16.7 | 28.6 |

7.4. In Vivo Efficacy of Humanized Anti-PD-1 Antibodies in the PD-1 Humanized Mouse Model Implanted Subcutaneously with MC38 Colon Cancer Cells The B-hPD-1 humanized mice were used to evaluate the in vivo efficacy of anti-human PD-1 antibodies. The B-hPD-1 mice were developed from the C57BL/6 genetic background mice by Beijing Biocytogen Co., Ltd. Using the gene targeting technique, the second exon portion of the PD-1 gene of the C57BL/6 mice, including the IgV domain portion, was replaced with the human PD-1 fragment. Successfully constructed mice could express human-mouse chimeric PD-1, which comprised the extracellular part of hPD-1 and the intracellular part of mPD-1. This type of chimeric PD-1 had normal signaling ability of PD-1, as the murine or human PD-L1 ligand could bind to this PD-1 receptor to inhibit T cell activity.

The mouse MC38 colon cancer cells (Shunran Shanghai Biotechnology Co., Ltd.) at $5 \times 10^5$ cells/0.1 mL were inoculated subcutaneously in the right front flank of the female B-hPD-1 humanized mice. When the tumor sizes reached to about 150 mm³, the mice were randomly classified into 3 groups, 8 mice per group, which were (1) solvent control group (PBS group), (2) AB12M4 treatment group, and (3) Keytruda control group (Merck, lot number 5SNL80505). Drug dose and administration volume for both of the groups (2) and (3) were 20 mg/kg and 10 mL/kg, respectively. For all the groups, the route of administration was intraperitoneal injection. The drugs were given once every 3 days and total 6 times continuously. The experiment was terminated 28 days after inoculation.

The maximal diameter (L) and minimal diameter (W) of the tumor were measured using a vernier caliper, and the tumor volume (V) was calculated by the formula $V = \frac{1}{2} (L \times W^2)$. The tumor volume was measured three times a week, and meantime, the mouse body weight was measured.

As shown in FIG. 14, at the end of the experiment, the average tumor volume in the solvent control group was 3405.2 mm³. The average tumor volumes in the AB12M4 treatment group and the Keytruda control group were 277.4 mm³ and 249 mm³, respectively, which indicated that AB12M4 had a significant anti-tumor effect, and its anti-tumor effect was comparable to that of Keytruda. In addition, throughout the course of the experiment, the animals were in good health and no animals died. At the end of the experiment, the body weight of each group increased, and there was no significant difference of body weight between the AB12M4 treatment group and the solvent control group (p>0.05), which indicated that the animals had good tolerance to AB12M4, and AB12M4 had no obvious toxic effect on the experimental animals.

All publications mentioned in the present invention are hereby incorporated by reference to the same extent as if each of the documents were individually recited for reference. In addition, it is to be understood that various changes and modifications may be made by those skilled in the art upon reading the above teachings of the present invention, which also fall within the scope of the claims appended hereto.

What is claimed is:

1. An anti-PD-1 antibody, comprising a heavy chain variable region and a light chain variable region, wherein:
   (i) the heavy chain variable region comprises a CDR-H1 comprising the amino acid sequence of SEQ ID NO: 1, a CDR-H2 comprising the amino acid sequence of SEQ ID NO: 3, and a CDR-H3 comprising the amino acid sequence of SEQ ID NO: 5; and
   (ii) the light chain variable region comprises a CDR-L1 comprising the amino acid sequence of SEQ ID NO: 7, a CDR-L2 comprising the amino acid sequence of SEQ ID NO: 9, and a CDR-L3 comprising the amino acid sequence of SEQ ID NO: 11.

2. The anti-PD-1 antibody of claim 1, wherein the antibody is a murine or chimeric antibody, and wherein the heavy chain variable region comprises a heavy chain FR region of murine IgG$_1$, IgG$_2$, IgG$_3$ or a variant thereof, and the light chain variable region comprises a light chain FR region of murine κ, λ chain, or a variant thereof.

3. The anti-PD-1 antibody of claim 2, wherein the heavy chain variable region comprises the amino acid sequence of SEQ ID NO: 13, and the light chain variable region comprises the amino acid sequence of SEQ ID NO: 14.

4. The anti-PD-1 antibody of claim 2, wherein the antibody is a humanized antibody.

5. The anti-PD-1 antibody of claim 4, wherein the heavy chain variable region comprises an amino acid sequence selected from the group consisting of SEQ ID NOs: 17, 19, 21, 23, 25, 27, and 29; and the light chain variable region comprises an amino acid sequence selected from the group consisting of SEQ ID NOs: 18, 20, 22, 24, 26, 28, and 30.

6. The anti-PD-1 antibody of claim 5, wherein:
the heavy chain variable region comprises the amino acid sequence of SEQ ID NO: 17, and the light chain variable region comprises the amino acid sequence of SEQ ID NO: 18;
the heavy chain variable region comprises the amino acid sequence of SEQ ID NO: 19, and the light chain variable region comprises the amino acid sequence of SEQ ID NO: 20;
the heavy chain variable region comprises the amino acid sequence of SEQ ID NO: 21, and the light chain variable region comprises the amino acid sequence of SEQ ID NO: 22;
the heavy chain variable region comprises the amino acid sequence of SEQ ID NO: 23, and the light chain variable region comprises the amino acid sequence of SEQ ID NO: 24;
the heavy chain variable region comprises the amino acid sequence of SEQ ID NO: 25, and the light chain variable region comprises the amino acid sequence of SEQ ID NO: 26;
the heavy chain variable region comprises the amino acid sequence of SEQ ID NO: 27, and the light chain variable region comprises the amino acid sequence of SEQ ID NO: 28; or
the heavy chain variable region comprises the amino acid sequence of SEQ ID NO: 29, and the light chain variable region comprises the amino acid sequence of SEQ ID NO: 30.

7. An anti-PD-1 antibody comprising a heavy chain variable region and a light chain variable region, wherein the heavy chain variable region comprises an amino acid sequence selected from the group consisting of SEQ ID NOs: 31, 33, and 35, and the light chain variable region comprises an amino acid sequence selected from the group consisting of SEQ ID NOs: 32, 34, and 36.

8. The anti-PD-1 antibody of claim 7, wherein:
the heavy chain variable region comprises the amino acid sequence of SEQ ID NO: 31, and the light chain variable region comprises the amino acid sequence of SEQ ID NO: 32;
the heavy chain variable region comprises the amino acid sequence of SEQ ID NO: 33, and the light chain variable region comprises the amino acid sequence of SEQ ID NO: 34; or
the heavy chain variable region comprises the amino acid sequence of SEQ ID NO: 35, and the light chain variable region comprises the amino acid sequence of SEQ ID NO: 36.

9. The anti-PD-1 antibody of claim 1, comprising a substitution of one or more amino acids compared to SEQ ID NOs: 17, 18, 19, 20, 21, 22, 23, 24, 25, 26, 27, 28, 29, or 30.

10. The anti-PD-1 antibody of claim 1, comprising at least 80%, 85%, 90%, 95%, 96%, 97%, 98%, or 99% amino acid sequence identity to the amino acid sequence of SEQ ID NOs: 17, 18, 19, 20, 21, 22, 23, 24, 25, 26, 27, 28, 29, or 30.

11. The anti-PD-1 antibody of claim 1, comprising a heavy chain constant region of human $IgG_4$ or $IgG_1$ and a human κ light chain constant region, or an antigen-binding fragment that is Fab, F(ab')2, or scFv.

12. The anti-PD-1 antibody of claim 1, wherein the antibody is glycosylated.

13. The anti-PD-1 antibody of claim 1, wherein the antibody binds to PD-1 with a KD of 1 nM or less.

14. A DNA molecule encoding the anti-PD-1 antibody of claim 1.

15. The DNA molecule of claim 14, wherein the DNA molecule comprises a first nucleic acid sequence encoding the heavy chain variable region of the antibody, wherein the first nucleic acid sequence is selected from the group consisting of SEQ ID NOs: 37, 39, and 41; and a second nucleic acid sequence encoding the light chain variable region of the antibody, wherein the second nucleic acid sequence is selected from the group consisting of SEQ ID NOs: 38, 40, and 42.

16. An expression vector comprising the DNA molecule of claim 14.

17. A host cell transformed with the expression vector of claim 16.

18. A bispecific molecule comprising the anti-PD-1 antibody of claim 1, wherein the bispecific molecule further comprises an antibody against a molecule selected from the group consisting of VEGF, EGFR, HER2/neu, VEGF receptor or other growth factor receptors, CD20, CD40, CTLA-4, OX-40, 4-1-BB, and ICOS.

19. An immunoconjugate comprising the anti-PD-1 antibody of claim 1 and a therapeutic agent.

20. A pharmaceutical composition comprising the anti-PD-1 antibody of claim 1 and a pharmaceutically acceptable excipient, carrier, and/or diluent.

21. A method for preparing an antibody, comprising culturing the host cell of claim 17 under conditions that allow production of the antibody, and recovering and isolating the antibody from the host cell.

22. A method of treating a subject suffering from a PD-1-mediated disease or condition, comprising administrating an effective amount of the anti-PD-1 antibody of claim 1 to the subject, wherein the PD-1-mediated disease or condition is lung cancer, liver cancer, ovarian cancer, cervical cancer, skin cancer, bladder cancer, colon cancer, breast cancer, glioma, kidney cancer, stomach cancer, esophageal cancer, oral squamous cell carcinoma, head and neck cancer, chronic viral infections, bacterial infections, or parasitic infections.

23. The anti-PD-1 antibody of claim 13, wherein the antibody binds to PD-1 with a KD of 100 pM or less.

24. The anti-PD-1 antibody of claim 13, wherein the antibody binds to PD-1 with a KD of 10 pM or less.

25. The anti-PD-1 antibody of claim 13, wherein the antibody binds to PD-1 with a KD of 1 pM or less.

26. The DNA molecule of claim 15, wherein the DNA molecule comprises a first nucleic acid sequence encoding the heavy chain variable region of the antibody and a second nucleic acid sequence encoding the light chain variable region of the antibody, and wherein:
  (a) the first nucleic acid sequence is SEQ ID NO: 37, and the second nucleic acid sequence is SEQ ID NO: 38;
  (b) the first nucleic acid sequence is SEQ ID NO: 39, and the second nucleic acid sequence is SEQ ID NO: 40; or
  (c) the first nucleic acid sequence is SEQ ID NO: 41, and the second nucleic acid sequence is SEQ ID NO: 42.

27. The immunoconjugate of claim 19, wherein the therapeutic agent is selected from the group consisting of a toxin, a radioisotope, a drug, and a cytotoxic agent.

* * * * *